(12) United States Patent
Mitalipov

(10) Patent No.: US 9,434,921 B2
(45) Date of Patent: Sep. 6, 2016

(54) METHODS FOR MITOCHONDRIAL DNA REPLACEMENT IN OOCYTES

(75) Inventor: Shoukhrat M. Mitalipov, Beaverton, OR (US)

(73) Assignee: Oregon Health & Science University, Portland, OR (US)

( * ) Notice: Subject to any disclaimer, the term of this patent is extended or adjusted under 35 U.S.C. 154(b) by 1139 days.

(21) Appl. No.: 13/265,326

(22) PCT Filed: Apr. 22, 2010

(86) PCT No.: PCT/US2010/032101
§ 371 (c)(1),
(2), (4) Date: Oct. 19, 2011

(87) PCT Pub. No.: WO2010/124123
PCT Pub. Date: Oct. 28, 2010

(65) Prior Publication Data
US 2012/0036591 A1 Feb. 9, 2012

Related U.S. Application Data

(60) Provisional application No. 61/172,644, filed on Apr. 24, 2009.

(51) Int. Cl.
| | |
|---|---|
| *A01K 67/027* | (2006.01) |
| *C12N 15/00* | (2006.01) |
| *C12N 5/075* | (2010.01) |
| *C12N 5/16* | (2006.01) |
| *C12N 15/877* | (2010.01) |
| *C12N 15/873* | (2010.01) |
| *C12N 5/073* | (2010.01) |

(52) U.S. Cl.
CPC ........... *C12N 5/0609* (2013.01); *C12N 5/0604* (2013.01); *C12N 5/16* (2013.01); *C12N 15/873* (2013.01); *C12N 15/8775* (2013.01); *C12N 15/8776* (2013.01); *C12N 2517/10* (2013.01)

(58) Field of Classification Search
CPC .............. C12N 5/0609; C12N 5/0604; C12N 15/8776
USPC .......................................................... 800/24
See application file for complete search history.

(56) References Cited

U.S. PATENT DOCUMENTS

| | | | |
|---|---|---|---|
| 6,252,133 B1 | 6/2001 | Campbell et al. | |
| 7,351,876 B2 | 4/2008 | Brem et al. | |
| 7,371,922 B2 | 5/2008 | Wheeler et al. | |
| 7,972,849 B2 | 7/2011 | Mitalipov et al. | |
| 2002/0056149 A1 | 5/2002 | Campbell et al. | |
| 2003/0229908 A1 | 12/2003 | Cibelli et al. | |
| 2009/0004740 A1 | 1/2009 | Mitalipov et al. | |
| 2010/0144549 A1 | 6/2010 | Mitalipov et al. | |

FOREIGN PATENT DOCUMENTS

| | | |
|---|---|---|
| WO | WO 03/057863 A2 | 7/2003 |
| WO | WO 03/057863 A3 | 7/2003 |
| WO | WO 2008/144580 A2 | 11/2008 |
| WO | WO 2008/144580 A3 | 11/2008 |

OTHER PUBLICATIONS

Tarkowski (J. Embryol, exp. Morph, 55:319-330.*
Wallace, 1988, Science, 242:1427-1430.*
Egli et al., "Developmental reprogramming after chromosome transfer into mitotic mouse zygotes," Nature 447(7145):679-685 (Jun. 7, 2007).
Li et al., "Human embryos derived by somatic cell nuclear transfer using an alternative enucleation approach," Cloning and Stem Cells 11(1):39-50 (Mar. 1, 2009).
Spikings et al., "Transmission of mitochondrial DNA following assisted reproduction and nuclear transfer," Human Reproduction Update 12(4):401-415 (Jan. 1, 2006).
St. John and Schatten "Paternal mitochondrial DNA transmission during nonhuman primate nuclear transfer," Genetics 167(2): 897-905 (Jun. 1, 2004).
Tachibana et al., "Mitochondrial gene replacement in primate offspring and embryonic stem cells," Nature 461(7262):367-372 (Aug. 26, 2009).
Tachibana et al., "Towards germline gene therapy of inherited mitochondrial diseases," Nature 493(7434):627-631 (Oct. 24, 2012).
Tanaka et al., "Metaphase II karyoplast transfer from human in-vitro matured oocytes to enucleated mature oocytes," Reproductive BioMedicine Online 19(4):514-520 (Oct. 1, 2009).
Zhang et al., "Pregnancy derived from human nuclear transfer," Fertility and Sterility 80(Suppl. 03):S56 (Jan. 9, 2003) (Abstract).
"An experimental method designed to fuse donor cells to mouse enucleated oocytes using inactivated Sendai virus (HVJ Envelope: HVJ-E)," Cosmo Bio Co., LTD. (downloaded on Jan. 26, 2009).
Bredenoord et al., "Dealing with uncertainties: ethics of prenatal diagnosis and preimplantation genetic diagnosis to preventmitochondrial disorders," Human Reproduction Update 14(1):83-94 (2008).
Bredenoord et al., "Ooplasmic and nuclear transfer to prevent mitochondrial DNA disorders: conceptual and normative issues," Human Reproduction Update 14(6):669-678 (2008).
Brown et al., "Transmission of mitochondrial DNA disorders: possibilities for the future," Lancet 368:87-89 (2006).
Fletcher-Holmes and Boutin, "User Protocol: Oosight™-Enabled Enucleation for Somatic Cell Nuclear Transfer," Oosight™ Imaging Systems (downloaded on Jan. 26, 2009).
Gropman, "Diagnosis and Treatment of Childhood Mitochondrial Diseases," Current Neurology and Neuroscience Reports 1:185-194 (2001).

(Continued)

Primary Examiner — Valarie Bertoglio
(74) Attorney, Agent, or Firm — Klarquist Sparkman, LLP

(57) ABSTRACT

Methods are provided for producing a primate oocyte in vitro. The methods include removing nuclear DNA from a recipient primate oocyte from a first primate in a manner that does not lower levels of maturation promoting factor (MPF) to form an enucleated recipient primate oocyte. The recipient primate oocyte is enucleated using a non-UV-based spindle imaging system. Nuclear genetic material or DNA including chromosomes from a donor primate oocyte arrested at metaphase II from a second primate is isolated in the form of the karyoplast and introduced into the enucleated recipient primate oocyte. Introduction of the chromosomes is performed using a fusogenic agent or electroporation to produce a hybrid oocyte.

16 Claims, 4 Drawing Sheets

(56) References Cited

OTHER PUBLICATIONS

International Search Report from parent PCT Application No. PCT/US2010/032101, 3pages (mailed Jun. 10, 2010).

Li et al., "In Vitro Development of Horse Oocytes Reconstructed with the Nuclei of Fetal and Adult Cells," *Biology of Reproduction* 66:1288-1292 (2002).

Liu et al., "Metaphase II nuclei generated by germinal vesicle transfer in mouse oocytes support embryonic development to term," *Human Reproduction* 18(9):1903-1907 (2003).

Liu et al., "Ooplasmic Influence on Nuclear Function During the Metaphase II-Interphase Transition in Mouse Oocytes," *Biology of Reproduction* 65:1794-1799 (2001).

"Ooplasm transfer as method to treat female infertility," *BRMAC Briefing Document* (for Day 1, May 9, 2002).

Roberts "Prevention of Human Mitochondrial (mtDNA) Disease by Nucleus Transplantation Into an Enucleated Donor Oocyte," *American Journal of Medical Genetics* 87:265-266 (1999).

Thorburn and Dahl, "Mitochondrial Disorders: Genetics, Counseling, Prenatal Diagnosis and Reproductive Options," *American Journal of Medical Genetics* (Semin. Med. Genet.) 106:102-114 (2001).

\* cited by examiner

FIG. 2A
FIG. 2B
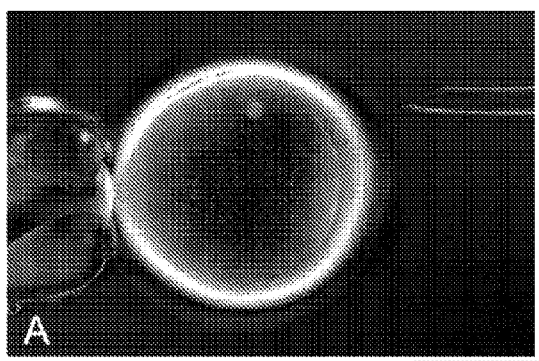
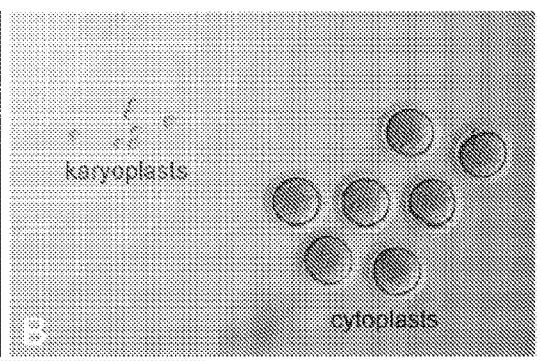
FIG. 2C
FIG. 2D
FIG. 2E
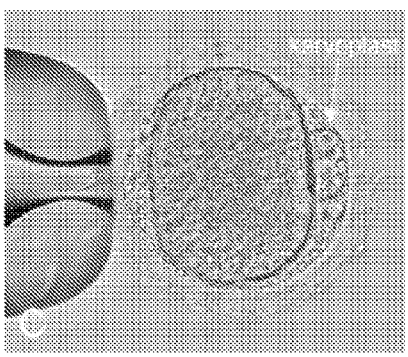
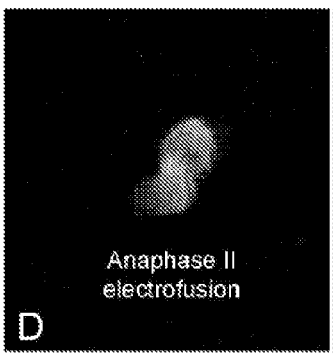
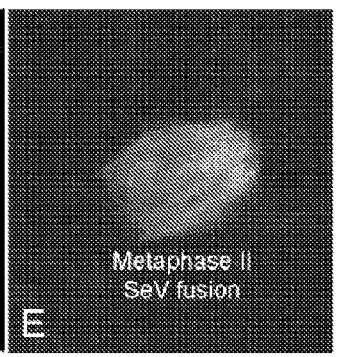

METHODS FOR MITOCHONDRIAL DNA REPLACEMENT IN OOCYTES

CROSS REFERENCE TO RELATED APPLICATIONS

This is the U.S. National Stage of PCT Application No. PCT/US2010/032101, filed Apr. 22, 2010, which was published in English under PCT Article 21(2), which in turn claims the benefit of U.S. Provisional Application No. 61/172,644, filed Apr. 24, 2009, which is incorporated by reference herein in its entirety.

STATEMENT OF GOVERNMENT SUPPORT

This invention was made with United States government support pursuant to grant RR00163, from the National Institutes of Health (NIH); the United States government has certain rights in the invention.

FIELD

This application relates to the field of in vitro fertilization, specifically to the production of oocytes for fertilization. The disclosed methods also provide a prenatal treatment method for mitochondrial disorders.

BACKGROUND

Mitochondria are found in all eukaryotic cells and are essential for basic cellular function due to their principal role in the production of energy. Mitochondria contain their own highly compact mitochondrial (mt)DNA encoding 37 intronless genes. Mutations in mtDNA occur at a 10-fold or higher rate than in nuclear DNA possibly due to the lack of histones and the very limited mtDNA repair mechanisms. Another contributing factor to mutations in mtDNA is a high concentration of free oxygen radicals.

Each mitochondrion contains between 2-10 copies of mtDNA; an individual cell may have several thousand copies of mtDNA. Homoplasty occurs when all mtDNA copies are identical within a cell. Occasionally, two or more types of mtDNA can co-exist within a cell as a mixture of mutant and normal mtDNA, a phenomenon known as heteroplasmy. Heteroplasmy allows lethal mutations to persist, but when the mutant mtDNA load reaches a certain threshold the mitochondrial function is impaired. This can lead to serious human disorders, including premature aging, myopathies, neurodegenerative diseases, diabetes, cancer and infertility.

It is estimated that at least 1 in 200 individuals have a mitochondrial DNA mutation that may lead to disease. Mitochondrial disorders or diseases attributable to defects in oxidative phosphorylation are mostly severe disorders and affect at least one in 8000 individuals (Chinnery et al., Ann Neurol, 2000. 48(2): p. 188-93). These conditions can be fatal or cause chronic morbidity. Mitochondrial disorders often affect the tissues that utilize the most ATP, such as the central nervous system, heart, skeletal muscles, liver and kidney (Gropman, Curr Neurol Neurosci Rep, 2001. 1(2): p. 185-94).

Mitochondrial diseases can be caused by genetic alterations of nuclear- or mitochondrial-encoded genes involved in the synthesis of ATP. While disorders resulting from nuclear DNA mutations follow a Mendelian pattern of autosomal recessive, dominant or X-linked inheritance, conditions that result from mtDNA defects have unique characteristics. Affected individuals are usually heteroplasmic: there is a mixture of normal and mutant mtDNA. The level of the mutant mtDNA can differ among tissues. If the mutant load (the ratio of mutant to normal mtDNA) exceeds a tissue- and individual-specific threshold, clinical features become evident, although exact genotype-phenotype correlations usually vary even within families (Chinnery et al., supra). Unlike the chromosomes, which are inherited both paternally and maternally, mtDNA is transmitted maternally (Giles et al., Proc Natl Acad Sci USA, 1980. 77(11): p. 6715-9). There is a significantly higher number of mtDNA molecules in a mature oocyte (200,000 to 300,000 copies) compared to the sperm (approximately 100 mtDNAs) (May-Panloup et al., Hum Reprod, 2005. 20(3): p. 593-7; Spikings, et al., Hum Reprod Update, 2006. 12(4): p. 401-15). Generally, sperm mitochondria that enter via fertilization are eliminated specifically during early embryo development (Sutovsky, et al., Nature, 1999. 402(6760): p. 371-2). There is a need for a feasible, efficacious and safe reproductive option designed to minimize the occurrence of mtDNA-defects in an embryo.

SUMMARY

Methods for the production of oocytes are disclosed herein. These methods can be used to produce viable oocytes, such as from individuals with mtDNA diseases. The oocytes can be from any mammal, such as a primate. The primate can be a human or a non-human primate.

In some embodiments, methods are provided for producing a mammalian oocyte in vitro. The methods include enucleating a recipient mammalian oocyte from a first mammal in a manner that does not lower levels of maturation promoting factor (MPF) to form an enucleated recipient mammal oocyte. In some examples, the recipient mammalian oocyte is enucleated using a non-UV-based spindle imaging system. Nuclear genetic material including chromosomes from a donor mammalian oocyte arrested at metaphase II from a second mammal, such as from the same species, is introduced into the enucleated recipient primate oocyte. Introduction of the chromosomes is performed using a fusogenic agent or electroporation to produce a hybrid oocyte. In several examples, the mammal is a human or a non-human primate.

In additional embodiments, the hybrid oocytes can be fertilized, so that viable offspring are produced. In other embodiments, the hybrid oocytes can be fertilized and cultured for the production of stem cells, including totipotent, pluripotent and multipotent stem cells. In one example, embryonic stem cells are produced. In some examples, the donor primate has a mitochondrial disease, and the recipient primate does not have the mitochondrial disease.

In further embodiments, methods are provided for producing an oocyte in vitro. The method includes enucleating a recipient primate oocyte from a first primate in a manner that does not lower levels of maturation promoting factor (MPF) wherein the primate oocyte is enucleated using a non-UV-based spindle imaging system. The recipient primate oocyte can be isolated from a subject without a mitochondrial disease. Chromosomes from a nuclear donor oocyte from a second donor primate, wherein the oocyte is arrested at metaphase II are isolated to form a karyoplast and introduced into the enucleated recipient primate oocyte. In some non-limiting examples, the donor primate has a mitochondrial disease. Introduction of the karyoplast is performed using a fusogenic agent, wherein the first primate and the second primate are from the same primate species.

The hybrid oocyte can be fertilized in vitro to produce a one-celled embryo. The one-celled embryo in vitro forms a two-, four- or eight-celled embryo, a morula or a blastocyst embryo.

The embryo can be introduced into a female and allowed to develop to term. Alternatively, the embryo can be used for the production of totitpotent, pluripotent, or multipotent stem cells.

In some embodiments, the methods disclosed herein can be used for providing prenatal treatment for a mitochodrial disorder.

The foregoing and other features and advantages will become more apparent from the following detailed description of several embodiments, which proceeds with reference to the accompanying figures.

BRIEF DESCRIPTION OF THE FIGURES

FIG. 2A-E are a set of digital images showing spindle transfer in MII oocytes. A-C, confocal microscopy of a monkey MII oocyte labeled with DAPI to depict chromosomes and with MitoTracker Red to label active mitochondria. B, karyoplasts and cytoplasts after enucleation. C, a karyoplast placed in perivitelline space of a cytoplast on the side opposite the 1st polar body before fusion. D, anaphase II after spindle transfer (ST) by electroporation. E, intact metaphase II spindle after spindle transfer produced by fusing with extract from Sendai virus SeV.

SEQUENCE LISTING

Figure 1:
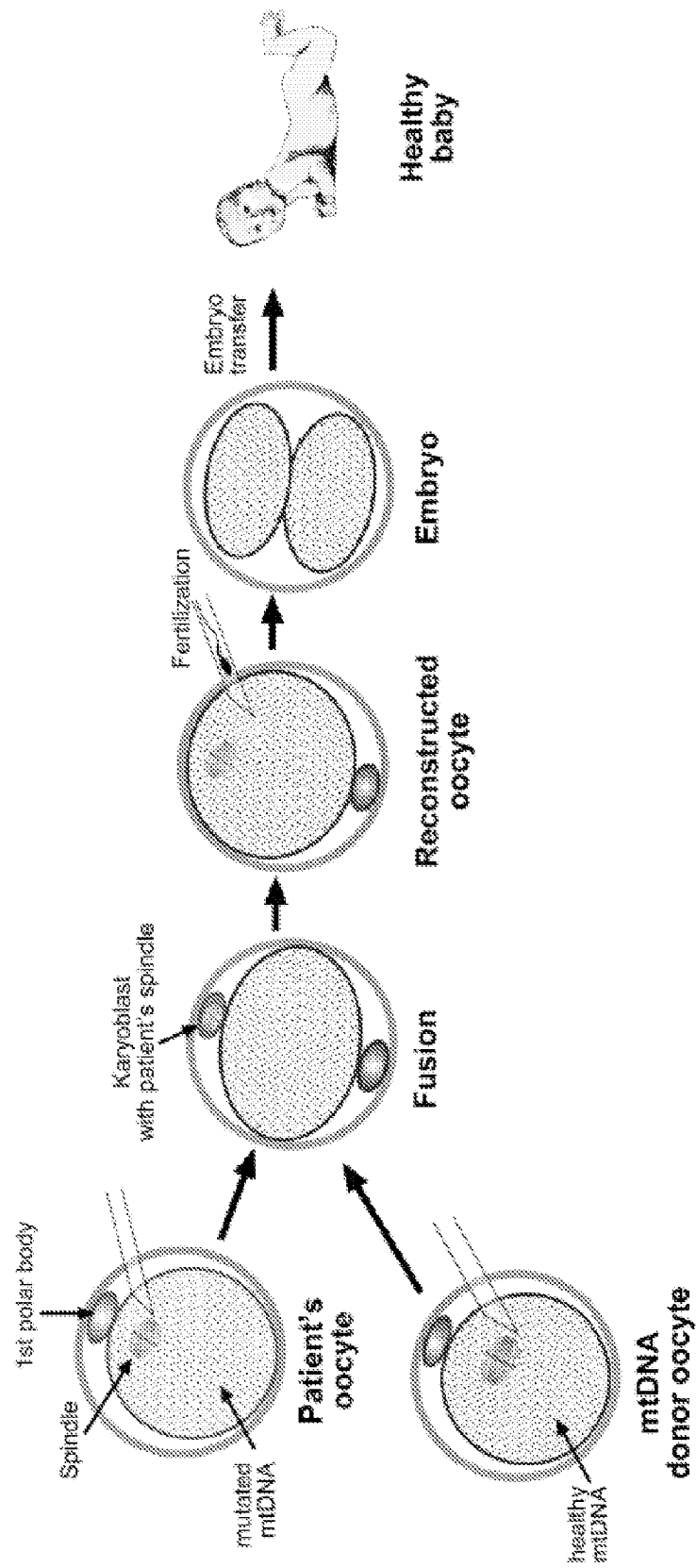
FIG. 1 is a schematic diagram representing mtDNA replacement in mature oocytes. The spindle (nuclear DNA) from a patient's egg carrying mtDNA mutations is removed and transplanted into an enucleated oocyte donated by a healthy donor. The reconstructed oocyte is then fertilized with the husband's sperm and an embryo is transferred to a patient. The infant will be free of risk from maternal mtDNA mutations.

The Sequence Listing is submitted as an ASCII text file 899-82614-09_Sequence_Listing.txt, Oct. 18, 2011, 702 bytes], which is incorporated by reference herein.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 and SEQ ID NO: 2 are the nucleic acid sequence of primers.

DETAILED DESCRIPTION

Over 150 mutations in mtDNA (including 100 deletions and approximately 50 point mutations) associated with human diseases have been identified (see for review, Solano, et al., Salud Publica Mex, 2001. 43(2): p. 151-61). Interest in their study has grown enormously due to the large number of patients diagnosed with these disorders and to the fact that they appear throughout life, from newborns to adults. The disorders include Leber's hereditary optic neuropathy (LHON), which can result from mutations in the gene for the NADH-Q oxidoreductase, component of complexes I and III. Myoclonic epilepsy with ragged-red fibres (MERRF) results in myoclonus, epilepsy and ataxia and is caused by mutations in tRNA genes. Some mitochondrial diseases are caused by large-scale deletions in mtDNA. The most known in this group is Kearns-Sayre Syndrome (KSS), which includes symptoms of pigment retinopathy and cardiac disorders. As indicated above, the clinical phenotypes resulting from mtDNA mutations are dependent on the proportion of mutated mtDNAs. In the case of LHON, >60% mutant mtDNA load is required before the disease phenotype presents. In other cases such as MERRF, over 85% mutant mtDNAs need to be present before symptoms are apparent.

At present, there are no cures for mitochondrial disorders and available treatments only improve symptoms and slow disease progression. Genetic counseling in patients at risk of maternally inherited mtDNA mutations is challenging due to limitations in assessing the extent of mtDNA heteroplasmy and accurately predicting risks. Hence, development of Assisted Reproductive Technologies (ARTs) to prevent mtDNA disease transmission in affected families is urgently needed. Currently, several conceptual ARTs could be used for mtDNA replacement including cytoplasmic transfer, germinal vesicle transfer, pronuclear transfer and blastomere nuclear transfer. However, all these techniques are associated with significant heteroplasmy due to mitochondrial carry over in the karyoplast. Moreover, these invasive protocols have not been evaluated extensively in animal models.

Thus, there is a need for a feasible, efficacious and safe reproductive option designed to minimize the occurrence of mtDNA-defects in an embryo. Disclosed herein are methods wherein mtDNA can be efficiently replaced in unfertilized oocytes by the transfer of nuclear genetic material in the form of metaphase chromosomes, also called "spindle transfer" (ST). The methods utilize mature metaphase II (MII) oocytes and do not interfere with subsequent nucleo-mtDNA compatibility and developmental competence after fertilization. Reconstructed oocytes produced by spindle transfer are nearly homoplasmic, containing healthy mtDNA and such oocytes retain their ability to support normal fertilization and full term development.

Thus, methods for the production of primate oocytes are disclosed herein. These methods can be used to produce developmentally competent primate oocytes, such as from individuals with mitochondrial (mt) DNA diseases. The primate can be a human or a non-human primate.

In some embodiments, the methods disclosed herein can be used for providing prenatal treatment for a mitochodrial disorder.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

DNA methylation: The postsynthetic addition of methyl groups to specific sites on DNA molecules; the reaction is catalyzed by enzymes called DNA methyltransferases that are specific for nucleotide and position of methylation. In eukaryotes, methylation is involved in gene expression, and plays a role in a variety of epigenetic mechanisms, including development, X chromosome inactivation, genomic imprinting, mutability of DNA, and uncontrolled cell growth in cancer. The term "X chromosome inactivation" refers to the inactivation of one of each pair of X chromosomes to form the Barr body in female mammalian somatic cells. Thus tissues whose original zygote carried heterozygous X borne genes should have individual cells expressing one or other but not both of the X encoded gene products. The inactivation is thought to occur early in development and leads to mosaicism of expression of such genes in the body.

Embryo: A cellular mass obtained by one or more divisions of a zygote or an activated oocyte with an artificially reprogrammed nucleus without regard to whether it has been implanted into a female. A "morula" is the preimplantation embryo 3-4 days after fertilization, when it is a solid mass, generally composed of 12-32 cells (blastomeres). A "blastocyst" refers to a preimplantation embryo in placental mammals (about 3 days after fertilization in the mouse, about 5 days after fertilization in humans) of about 30-150 cells. The blastocyst stage follows the morula stage, and can be distinguished by its unique morphology. The blastocyst is generally a sphere made up of a layer of cells (the trophectoderm), a fluid-filled cavity (the blastocoel or blastocyst cavity), and a cluster of cells on the interior (the inner cell mass, ICM). The ICM, consisting of undifferentiated cells, gives rise to what will become the fetus if the blastocyst is implanted in a uterus.

Feeder layer: Non-proliferating cells (such as irradiated cells) that can be used to support proliferation of stem cells. Protocols for the production of feeder layers are known in the art, and are available on the internet, such as at the National Stem Cell Resource web site, which is maintained by the American Type Culture Collection (ATCC).

Fusogenic agent: A chemical or biological agent that induces membrane fusion. Fusogenic agents include an extract from Sendai virus and polyethylene glycol. Electroporation can also induce fusion.

Genomic imprinting: A mammalian epigenetic phenomenon whereby the parental origin of a gene determines whether or not it will be expressed. Over 75 imprinted genes have been identified, many of which are noncoding RNAs that are hypothesized to control the expression of linked protein coding genes that are also imprinted. Generally, allele-specific methylation of CpG dinucleotides is a mechanism that regulates gene expression of imprinted genes. "Maternally expressed" refers to a gene that is expressed from the copy inherited from the mother. Imprinted genes include, but are not limited to the maternally expressed imprinted genes H19, CDKNIC, PHLDA2, DLX5, ATP10A, SLC22A18 or TP73. Paternally expressed imprinted genes include but are not limited to IGF2, NDN, SNRPN, MEST, MAGEL2, and PEG3. Exemplary sequence information for these genes, including the human nucleic acid sequences, can be found at the geneimprint website (© 2006), available on the internet; this information is incorporated by reference herein.

In Vitro Fertilization: The fusion of an oocyte and a sperm in culture outside of body, such that a one-celled embryo is formed. In vitro fertilization includes techniques wherein sperm is incubated with eggs in culture to form a one-celled embryo. Intracytoplamic Sperm Injection (ICSI) is an alternative in vitro fertilization procedure in which a single sperm is injected directly into an egg. The procedure is done under a microscope using micromanipulation devices. A holding pipette is used to stabilize the mature oocyte with gentle suction applied by a microinjector. From the opposite side a thin, hollow glass micropipette is used to collect a single sperm, having immobilized it by striking its tail with the point of the micropipette. The micropipette is pierced through the oolema and into the inner part of the oocyte (cytoplasm). The sperm is then released into the oocyte.

Karyoplast: Isolated nuclear material including the chromosomes, such as from an oocyte. The karyoplast includes the nuclear DNA encapsulated by nuclear membrane or nuclear DNA in the form of metaphase chromosomes without the nuclear membrane but surrounded by a small amount of cytoplasm and a cell membrane.

Lamin: The major non-collagenous component of the basal laimina. It is a glycoprotein that has an "A" chain and two "B" chains. Lamins are fibrous proteins providing structural function and transcriptional regulation in the cell nucleus. A-type lamins are only expressed following gastrulation. Lamin A and C are the most common A-type lamins and are splice variants of the LMNA gene.

Maturation promoting factor (MPF): A heterodimeric protein comprising cyclin B and cyclin-dependent kinase 1 (i.e., p34cdc2) that stimulates the mitotic and meiotic cell cycles. MPF promotes the entrance into mitosis from the G2 phase by phosphorylating multiple proteins needed during mitosis. MPF is activated at the end of G2 by a phosphatase which removes an inhibitory phosphate group added earlier. Targets for MPF include condensins, which enable chromatin condensation; various microtubule-associated proteins involved in mitotic spindle formation; lamins, whose interaction contribute to the degradation of the nuclear envelope as well as the histones, H1 and H3; and the Golgi matrix, to cause fragmentation (Nigg 1993; Szollosi, Czolowska et al., 1988).

Mitotic or Meiotic Spindle: The structure that separates the chromosomes into the daughter cells during cell division. It is part of the cytoskeleton in eukaryotic cells. Depending on the type of cell division, it is also referred to the meiotic spindle during meiosis. The cellular spindle apparatus includes the spindle microtubules, associated proteins, and any centrosomes or asters present at the spindle poles. The spindle apparatus is vaguely ellipsoid in shape and tapers at the ends but spreads out in the middle. In the wide middle portion, known as the spindle midzone, antiparallel microtubules are bundled by kinesins. At the pointed ends, known as spindle poles, microtubules are nucleated by the centrosomes in most animal cells.

Meiosis: A process of reductional division in which the number of chromosomes per cell is halved. In animals, meiosis always results in the formation of gametes.

During meiosis, the genome of a diploid germ cell, which is composed of long segments of DNA packaged into chromosomes, undergoes DNA replication followed by two rounds of division, resulting in four haploid cells. Each of these cells contain one complete set of chromosomes, or half of the genetic content of the original cell. Meiosis I separates homologous chromosomes, producing two haploid cells (23 chromosomes, N in humans), so meiosis I is referred to as a reductional division. A regular diploid human cell contains 46 chromosomes and is considered 2N because it contains 23 pairs of homologous chromosomes. However, after meiosis I, although the cell contains 46 chromosomes it is only considered N because later in anaphase I the sister chromatids will remain together as the spindle pulls the pair toward the pole of the new cell. In meiosis II, an equational division similar to mitosis occurs whereby the sister chromatids are finally split, creating a total of 4 haploid cells (23 chromosomes, N) per daughter cell from the first division.

Thus, meiosis II is the second part of the meiotic process. Much of the process is similar to mitosis. The end result is production of four haploid cells (23 chromosomes, 1N in humans) from the two haploid cells (23 chromosomes, 1N * each of the chromosomes consisting of two sister chromatids) produced in meiosis I. The four main steps of Meiosis II are: Prophase II, Metaphase II, Anaphase II, and Telophase II. In metaphase II, the centromeres contain two kinetochores that attach to spindle fibers from the centrosomes (centrioles) at each pole. The new equatorial metaphase plate is rotated by 90 degrees when compared to meiosis I, perpendicular to the previous plate.

Mitochondrial DNA or mtDNA: The DNA of the mitochondrion, a structure situated in the cytoplasm of the cell rather than in the nucleus (where all the other chromosomes are located). In vivo, all mtDNA is inherited from the mother. There are 2 to 10 copies of the mtDNA genome in each mitochondrion. mtDNA is a double-stranded, circular molecule. It is very small relative to the chromosomes in the nucleus and includes only a limited number of genes, such as those encoding a number of the subunits in the mitochondrial respiratory-chain complex and the genes for some ribosomal RNAs and transfer RNAs. A cell includes mtDNA derived from the continued replication cytoplasmically based mitochondria, which in the case of spindle transfer are based in the recipient cytoplast.

Mitochondrial Disease: Those disorders that affect the function of the mitochondria and/or are due to mitochondrial DNA. The mtDNA is exclusively maternally inherited. Generally these diseases are due to disorders of oxidative phosphorylation. Mitochondrial diseases are often cause by a pathogenic mutation in a mitochondrial gene. The mutations are usually heteroplasmic so there is a mixture of normal and mutant DNA, the level of which can differ among tissues. However, some of the mutations are homoplasmic, so they are present in 100% of the mtDNA. The percentage heteroplasmy of point mutations in the offspring is related to the mutation percentage in the mother. There is a genetic bottleneck, which occurs during oocyte development.

Leber's hereditary optic neuropathy (LHON) or Leber optic atrophy is a mitochondrially inherited (mother to all offspring) degeneration of retinal ganglion cells (RGCs) and their axons that leads to an acute or subacute loss of central vision; this affects predominantly young adult males. However, LHON is only transmitted through the mother as it is primarily due to mutations in the mitochondrial (not nuclear) genome and only the egg contributes mitochondria to the embryo. LHON is usually due to one of three pathogenic mitochondrial DNA (mtDNA) point mutations. These mutations are at nucleotide positions 11778 G to A, 3460 G to A and 14484 T to C, respectively in the ND4, ND1 and ND6 subunit genes of complex I of the oxidative phosphorylation chain in mitochondria. Clinically, there is an acute onset of visual loss, first in one eye, and then a few weeks to months later in the other. Onset is usually young adulthood, but age range at onset from 8-60 is reported. This typically evolves to very severe optic atrophy and permanent decrease of visual acuity.

Leigh's disease, also known as Subacute Necrotizing Encephalomyelopathy (SNEM), is a rare neurometabolic disorder that affects the central nervous system. It is an inherited disorder that usually affects infants between the age of three months and two years, but, in rare cases, teenagers and adults as well. In the case of the disease, mutations in mitochondrial DNA (mtDNA) or in nuclear DNA (gene SURF and some COX assembly factors) cause degradation of motor skills and eventually death. The disease is most noted for its degradation in one's ability to control one's movements. As it progresses rapidly, the earliest signs may be poor sucking ability and loss of head control and motor skills. Other symptoms include loss of appetite, vomiting, irritability, continuous crying (in infants), and seizures. A later sign can also be episodes of lactic acidosis, which can lead to impairment of respiratory and kidney function. Some children can present with loss of development skills or developmental regression and have often had investigations for failure to thrive. As the disease progresses in adults, it may also cause general weakness, kidney failure, and heart problems. Life expectancy is usually about a year within the onset of symptoms although both acute fulminating illness of a few days and prolonged survival have been reported.

Neuropathy, ataxia, and retinitis pigmentosa (NARP) is a condition that causes a variety of signs and symptoms chiefly affecting the nervous system. Beginning in childhood or early adulthood, most people with NARP experience numbness, tingling, or pain in the arms and legs (sensory neuropathy); muscle weakness; and problems with balance and coordination (ataxia). Many affected individuals also have vision loss caused by changes in the light-sensitive tissue that lines the back of the eye (the retina). In some cases, the vision loss results from a condition called retinitis pigmentosa. This eye disease causes the light-sensing cells of the retina gradually to deteriorate. Neuropathy, ataxia, and retinitis pigmentosa is a condition related to mutations in mitochondrial DNA, specifically in the MT-ATP6 gene.

Myoneurogenic gastrointestinal encephalopathy or MNGIE is another mitochondrial disease typically appearing between the second and fifth decades of life. MNGIE is a multisystem disorder causing ptosis, progressive external ophthalmoplegia, gastrointestinal dysmotility (often pseudoobstruction), diffuse leukoencephalopathy, thin body habitus, peripheral neuropathy, and myopathy.

Nuclear genetic material: Structures and/or molecules found in the nucleus which comprise polynucleotides (e.g., DNA) which encode information about the individual. Nuclear genetic material includes the chromosomes and chromatin. The term also refers to nuclear genetic material (e.g., chromosomes) produced by cell division such as the division of a parental cell into daughter cells. Nuclear genetic material does not include mitochondrial DNA.

Nuclear transfer: The transplantation of a donor nucleus into an enucleated recipient host cell. The transfer of nuclear genetic material attached to the meiotic or mitotic spindle can be referred to as "spindle transfer" or "ST." Spindle transfer includes the transfer of nuclear genetic material of a donor into a recipient cell, such as an oocyte. "Nuclear genetic material" includes chromosomal DNA.

Oocyte: a female gamete or germ cell involved in reproduction, also called an egg. A mature egg has a single set of maternal chromosomes (23, X in a human primate) and is halted at metaphase II. A "hybrid" oocyte has the cytoplasm from a first primate oocyte (termed a "recipient") but does not have the nuclear genetic material of the recipient; it has the nuclear genetic material from another oocyte, termed a "donor."

Prenatal: Existing or occurring before birth. Similarly, "postnatal" is existing or occurring after birth.

Primate: All animals in the primate order, including monkeys and humans. Exemplary non-human primates include, for example, chimpanzees, rhesus macaques, squirrel monkeys, lemurs. They include Old World, New World, and prosimian monkeys.

Telomere: The sequences and the ends of a eukaryotic chromosome, consisting of many repeats of a short DNA sequence in specific orientation. Telomere functions include protecting the ends of the chromosome, so that chromosomes do not end up joined together, and allowing replication of the extreme ends of the chromosomes (by telomerase). The number of repeats of telomeric DNA at the end of a chromosome decreases with age and telomeres may play roles in aging and cancer. "Telomerase" refers to a DNA polymerase involved in the formation of telomeres and the maintenance of telomere sequences during chromosome replication.

Totipotent or totipotency: A cell's ability to divide and ultimately produce an entire organism including all extra-embryonic tissues in vivo. In one aspect, the term "totipotent" refers to the ability of the cell to progress through a series of divisions into a blastocyst in vitro. The blastocyst comprises an inner cell mass (ICM) and a trophectoderm. The cells found in the ICM give rise to pluripotent stem cells (PSCs) that possess the ability to proliferate indefinitely, or if properly induced, differentiate in all cell types contributing to an organism. Trophectoderm cells generate extra-embryonic tissues, including placenta and amnion.

As used herein, the term "pluripotent" refers to a cell's potential to differentiate into cells of the three germ layers: endoderm (e.g., interior stomach lining, gastrointestinal tract, the lungs), mesoderm (e.g., muscle, bone, blood, urogenital), and ectoderm (e.g., epidermal tissues and nervous system). Pluripotent stem cells can give rise to any fetal or adult cell type including germ cells. However, PSCs alone cannot develop into a fetal or adult animal when transplanted in utero because they lack the potential to contribute to all extraembryonic tissue (e.g., placenta in vivo or trophoblast in vitro).

PSCs are the source of multipotent stem cells (MPSCs) through spontaneous differentiation or as a result of exposure to differentiation induction conditions in vitro. The term "multipotent" refers to a cell's potential to differentiate and give rise to a limited number of related, different cell types. These cells are characterized by their multi-lineage potential and the ability for self-renewal. In vivo, the pool of MPSCs replenishes the population of mature functionally active cells in the body. Among the exemplary MPSC types are hematopoietic, mesenchymal, or neuronal stem cells.

Transplantable cells include MPSCs and more specialized cell types such as committed progenitors as well as cells further along the differentiation and/or maturation pathway that are partly or fully matured or differentiated. "Committed progenitors" give rise to a fully differentiated cell of a specific cell lineage. Exemplary transplantable cells include pancreatic cells, epithelial cells, cardiac cells, endothelial cells, liver cells, endocrine cells, and the like.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Amounts that are "about" a given numeric range or value include the exact numeric range or value. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limitin Methods for Producing Reconstructed Oocytes Methods are provided herein for manipulating an oocyte in vitro. These methods include enucleating a recipient oocyte from a first mammal in a manner that does not lower levels of maturation promoting factor (MPF) to form an enucleated cell (or cytoplast), wherein the recipient oocyte is enucleated using a non-UV-based spindle imaging system. Nuclear genetic material comprising chromosomes from a donor oocyte arrested at metaphase II from a second mammal is isolated and introduced into the enucleated recipient oocyte.

Generally, introduction of the chromosomes is performed using a fusogenic agent or electroporation, to produce a hybrid oocyte. The first mammal and the second mammal can be from any mammalian species, including human and nonhuman animals. Generally, the recipient and the donor are from the same species. However, the recipient and the donor can be from two different species. The mammals can be primates, including non-human primates or humans. In some examples, the first mammal and the second mammal are primates of the same species. In some examples, the first mammal and the second mammal are humans. In other examples the first mammal and the second mammal are both primates, but from different species, such as a rhesus monkey and a baboon.

In one embodiment, the recipient primate oocyte is from a subject who does not have a mitochondrial DNA mutation, such as a homoplasmic or heteroplasmic mitochondrial disease. This can be determined, for example, by genetic assay, such as by assessing the mitochondrial DNA, or it can be determined by clinical evaluation. The nuclear genetic material such as the chromosomes can be isolated from a donor oocyte from a subject, such as a primate subject, with a mitochondrial DNA disease, such as a homoplasmic or heteroplasmic mitochondrial disease. In some embodiments, the mitochondrial disease can be associated with infertility. Examples of mitochondrial disease associated with infertility include Leber's hereditary optic neuropathy, myoclonic epilepsy, or Kearns-Sayre Syndrome. Thus in some examples, a recipient primate oocyte is from a subject that does not have Leber's hereditary optic neuropathy, myoclonic epilepsy, or Kearns-Sayre Syndrome. In other example, the nuclear genetic material including the chromosomes is from a donor primate oocyte from a primate subject that has Leber's hereditary optic neuropathy, myoclonic epilepsy, Neuropathy, ataxia and pigmentary retinopathy syndrome, Maternally inherited Leigh's syndrome (MILS), Myoclonic epilepsy syndrome with red-ripped fibers (MERRF), Mitochondrial encephalo-myopathy syndrome with lactic acidosis and cerebro-vascular accident episodes (MELAS), Maternally inherited diabetes with deafness, mitochondrial encephalomyopathy, chronic progressive external opthalmoplegia, Pearson's bone marrow-pancreas syndrome, diabetes insipidus, diabetes mellitus, optic atrophy and deafness (DIDMOAD), Chronic progressive external opthalmoplegia or Kearns-Sayre's Syndrome. Thus, the recipient primate oocyte is isolated from a subject that does not have mitochondrial disease, such as Leber's hereditary optic neuropathy, myoclonic epilepsy, Neuropathy, ataxia and pigmentary retinopathy syndrome, Maternally inherited Leigh's syndrome (MILS), Myoclonic epilepsy syndrome with red-ripped fibers (MERRF), Mitochondrial encephalo-myopathy syndrome with lactic acidosis and cerebro-vascular accident episodes (MELAS), Maternally inherited diabetes with deafness, mitochondrial encephalomyopathy, chronic progressive external opthalmoplegia, Pearson's bone marrow-pancreas syndrome, diabetes insipidus, diabetes mellitus, optic atrophy and deafness (DIDMOAD), Chronic progressive external opthalmoplegia and Kearns-Sayre's Syndrome.

The methods include transferring nuclear genetic material including the chromosomes, such as by performing a spindle transfer. The nuclear genetic material can be from any subject of interest. In several embodiments, the methods include the use of human or non-human primate oocytes.

In one embodiment, the donor nuclear genetic material including chromosomes also can include modified nucleic acids, such as nucleic acid (e.g., DNA) that includes a recombinant product, for example from a transgenic non-human primate. In one non-limiting example, the donor nuclear genetic material is obtained from a transgenic animal or an animal, such as a non-human primate with an engineered knock-out mutation. In a further example, the donor nuclear genetic material includes heterologous nucleic acid that encodes a protein product, such as a detectable marker, enzyme, or other protein. The donor nuclear genetic material including the chromosomes can also include other heterologous nucleic acids, such as ribozymes or antisense nucleic acid sequences. The heterologous nucleic acid can also include a regulatory sequence, such as a promoter, enhancer, insulator or repressor. Techniques for modifying nucleic acids are well known in the art, and include inserting a DNA that is synthetic or from another organism into the donor nucleic acid of the nuclear genetic material, deleting one or more DNA sequences from the donor, and introducing mutations, such as point mutations into the donor nucleic acid.

Methods and tools for manipulation of nucleic acids are well known in the art, see for example *Molecular Cloning: A Laboratory Manual*, second edition (Sambrook et al., 1989) Cold Spring Harbor Press; *Oligonucleotide Synthesis* (M. J. Gait, ed., 1984); Animal Cell Culture (R. I. Freshney), ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991) *Short Protocols in Molecular Biology* (Wiley and Sons, 1999), *Embryonic Stem Cells: A Practical Approach* (Notaranni et al. eds., Oxford University Press 2006); and *Essential of Stem Cell Biology* (R. Lanza, ed., Elsevier Academic Press 2006).

For enucleation, high quality recipient primate oocytes can be used. High quality primate oocytes can be obtained by using protocols that stimulate the animal (e.g., primates) to produce a number of viable oocytes. Examples of such stimulation protocols are disclosed in the Examples Section below and also in Zelinski-Wooten, et al. *Hum. Reprod.* 10:1658-1666 (1995). The method of harvesting can also be important in obtaining high-quality oocytes. In one example, the primate oocytes can be harvested using methods known in the art, such as follicular aspiration, and then separated from contaminating blood cells. As an alternative, primate oocytes can be generated from pluripotent stem cells in vitro.

In one aspect, when primates are stimulated to produce oocytes (such as hormonally) and these oocytes are harvested, the oocytes that are collected can be in different phases. Some oocytes are in metaphase I while other oocytes are in metaphase II. In such cases, the oocytes that are in metaphase I can be put into culture until they reach metaphase II and then used for enucleation to serve as the host cell. Optionally, the oocytes that have been cultured to reach metaphase II are combined with the oocytes that were already at metaphase II when harvested for a pool of potential host cells. In other cases, only the oocytes that are in metaphase II from the harvest are used for enucleation. Any of these oocytes can be frozen for further use. Thus, the donor and/or the recipient oocyte can be cryopreserved prior to use.

In some embodiments, the enucleation of the recipient cell is accomplished using a technique that avoids an inhibition or down-regulation of maturation promoting factor (MPF) or its activity. The enucleation of the recipient cell refers to meiotic spindle removal. Maturation promoting factor or MPF is a heterodimeric protein comprising cyclin B and cyclin-dependent kinase 1 (i.e., p34cdc2) that stimulates the mitotic and meiotic cell cycles. Without being bound by theory, MPF promotes the entrance into mitosis from the G2 phase by phosphorylating multiple proteins needed during mitosis. In some embodiments, the technique results in a decrease of MPF concentration and/or activity by less than about 5%, less than about 10%, less than about 15%, less than about 20%, or less than about 25%. In this context, "about" indicates within 1-2% of the designated value. Methods can also be used to increase MPF activity or concentration, as discussed below.

The technique employed to enucleate the recipient cell and isolate a nuclear material or karyoplast from the donor cell can be any imaging system that avoids reducing the MPF levels or activity. MPF activity or levels can be determined by looking for biological effects that indicate activation has occurred. This would include resumption and completion of meiosis. It is further contemplated that the spindle transfer techniques useful in the method provided herein include not only those that directly impact MPF levels or activity, but also those that indirectly affect MPF levels or activity.

In some embodiments, removal of nuclear genetic material (i.e., enucleation) from the recipient cell and isolation of genetic material from the donor cell is accomplished without lowering the levels of maturation promoting factor (MPF) or its activity. In one embodiment, this means that the enucleation and the karyoplast isolation are accomplished without the use of UV-based methods, such as Hoechst 33342 staining and subsequent UV visualization. One method that can be used in lieu of Hoechst 33342 is real time spindle imaging. In one embodiment, the enucleation and karyoplast isolation techniques employ the real time spindle imaging system such as OOSIGHT™ Imaging System (CRI, Inc. Woburn, Mass.). This system utilizes a wavelength of 545 nm and has diffraction limited spatial resolution. The relay optics are 0.65×. Generally the system includes a circular polarized interference filter with tunable liquid crystal polarizing filters. In one example, any system is of use that utilizes a liquid crystal tunable fiberoptic, a circular polarizer/green interference fiber optic, and can include a CCD camera with software for image acquisition and analysis. Generally, the system can merge polarized light imaging with single point analysis by quantifying magnitude and orientation of birefringence at each pixel in a field, at or near to real time. The spindle and the zona pellucida of an oocyte display an intrinsic property termed "birefringence" when trans-illuminated with polarized light, a property that can be used for efficient spindle visualization and thus enucleation or karyoplast isolation. The use of such a real time system permits non-invasive visualization and the complete, or essentially complete, removal of nuclear material from the host cell (e.g., an oocyte). In one example, the entire mitotic spindle and its associated DNA from the host cell is removed such that any potential for generating abnormal ploidy embryos is reduced or eliminated altogether. This system also allows isolation of an intact spindle and chromosomes from the donor oocyte into a karyoplast and subsequent transplantation of a karyoplast into an enucleated recipient oocyte, thereby transferring nuclear genetic material into the enucleated recipient oocyte.

In addition, exposure to caffeine, a protein phosphatase inhibitor (Kawahara et al., Reproduction 130(3): 351-7, 2005; Lee and Campbell, Biol Reprod 74(4): 691-8, 2006) or the proteasome inhibitor, MG-132 (Zhou et al., Science 302(5648): 1179, 2003) increases the activity of MPF. MG-132 can be utilized in the methods disclosed herein at concentrations, for example, of about 0.1 to 10 µM, such as about 0.5 to about 10 µM, such as about 0.5 to about 5 µM, such as about 1 to about 3 µM, such as about 1 to about 2 µM. In some examples, 0.2, 2 or 5 µM MG-132 can be utilized. Caffeine can be used, for example at concentrations of about 0.25 mM to about 25 mM, such as about 1 mM to 10 mM, such as 1 mM to 3 mM, such as about 2.5 mM.

In another embodiment, for either the enucleation step or the spindle isolation and transfer step or both, the use of any suitable reagent that minimizes calcium fluxes in the recipient oocyte and karyoplast immediately following spindle transfer can be employed. Without being bound by theory, the reduction of calcium fluxes following spindle transfer maintains spindle integrity. In one aspect, the avoidance of calcium fluxes or oscillation in the recipient oocyte cell allows for the MPF levels to be kept high and thus prevents premature activation and resumption of meiosis.

In several examples, enucleation and/or spindle transfer is performed in calcium ($Ca^{2+}$)-free media. For example, fusion of the karyoplast and cytoplast can be achieved in calcium-free fusion buffer. This media is substantially free of calcium ions. In one embodiment, a calcium-free medium contains less than about $10^{-6}$ M calcium cations ($Ca^{2+}$), such a media that contains less that as $10^{-7}$ M calcium cations, $10^{-8}$ M calcium cations, $10^{-9}$ M calcium cations, or is substantially free of calcium cations. Similarly, a magnesium-free medium contains less than about $10^{-6}$ M magnesium cations ($Mg^{2+}$), such a media that contains less that as $10^{-7}$ M magnesium cations, $10^{-8}$ M magnesium cations, $10^{-9}$ M magnesium cations, or is substantially free of magnesium cations. The selection of the appropriate media or other reagents that will, for example, chelate extracellular calcium and/or magnesium, such as ethylene glycol tetraacetic acid (EGTA) or ethylene diamine tetraacetic acid (EDTA), do not have added calcium and/or magnesium ions, or otherwise reduce the calcium fluxes during these manipulations are known in the art. Exemplary media are described in the examples section. These media and reagents are commercially available, and suitable media can be routinely produced in the laboratory. Methods for electrofusion are disclosed, for example, in U.S. Patent Application Publication No. 2009/0004740, which is incorporated herein by reference with regard to all the methods disclosed therein. However, in some examples, electrofusion is not utilized.

In some embodiments, the nuclear genetic material including the chromosomes (e.g., a karyoplast) from the donor oocyte can be introduced into the recipient oocyte by any method known to one of skill in the art. In some examples, electrofusion is not utilized. Thus, spindle transfer can be achieved. The nuclear genetic material can be introduced using micromanipulation techniques. The karyoplast can be pushed with the aid of a suitable apparatus, such as a transfer pipette, under the zona pellucida of the enucleated oocyte and deposited therein. In some examples, such as for use in non-human oocytes, a sharp beveled enucleation pipette (25-27 um outer diameter) is used to pierce through the zona pellucida. In additional embodiments, such as for use with primate oocytes, laser assisted zona drilling or Piezo drilling can be performed. Systems for laser assisted zona drilling are commercially available and include XYCLONE® or the ZILOS-TK™ laser system (Hamilton Thorne, Inc.) The XYCLONE® components include a laser, a collimating lens, a dichroic mirror, and an objective that can transmit the beam. The system includes: (1) Laser: 1480 µm, Infrared Class 1, the Collimating Lens: A lens used to produce a beam of parallel light rays; (2) Dichroic Mirror: An optical device which acts like an optical gate to split light into two colors that reflects the infrared laser beam up through the objective, while the visible light passes through; (3) Objective lens: allows transmission of laser beam to the sample. Protocols for the use of this system are available, such as Turetsky et al., Human Reproduction. Advanced Access, November 2007, doi:10.1093/humrep/dem351; Hall et al., Human Reproduction, 2007. Jan. 22(1): 52-62.

For integration of the nuclear genetic material including chromosomes into the ovum, the membrane of the karyoplast can be fused with the membrane of the recipient enucleated oocyte using a fusogenic agent. For example, fusion using the Sendai virus extract, treatment with PEG (polyethylene glycol) or laser-assisted fusion can be utilized.

Exposure of cells to fusion-promoting chemicals such as polyethylene glycol or other glycols is a routine procedure for the fusion of somatic cells (see for example, U.S. Pat. No. 6,252,133). As polyethylene glycol is toxic it is necessary to expose the cells for a minimum period and the need to be able to remove the chemical quickly may necessitate the removal of the zona pellucida (Kanka et al., Mol. Reprod. Dev. 29 110-116, 1991). In an exemplary protocol, PEG (molecular weight 1,300-1,600 Sigma), is mixed in a solution containing TL HEPES (approximately 1:0.25 µg/ml) and polyvinyl alcohol (PVA) (approximately 1 µg/ml), $Ca^{2+}$ and $Mg^{2+}$-free. The media containing the oocytes is then passed through one or more dilutions (approximately 1:1) of the above-described PEG media.

Inactivated Sendai virus (also called "HVJ") also provides an efficient means for the fusion of cells from cleavage-stage embryos (Graham Wistar enst. Symp. Monogr. 9-19, 1969), with the additional experimental advantage that activation is not induced. Inactivated Sendai virus envelope protein can also be used. Reagents for fusion using inactivated Sendai virus are commercially available, such as GENOMONE™ kit (Cosmo Bio. Co. Ltd.). Protocols are well known in the art (see Kato and Tsunoda, "Protocol 9: Inactivated Sendai Fusion", in Embryonic Stem Cells: A Practical Approach, Notarianni and Martin Eds.), Oxford University Press, 2006 or "Membrane fusion" By Jan Wilschut, Dick Hoekstra, CRC Press, 1990. ISBN 0824783018, 9780824783013). A well-recognized use for SeV is the fusion of eukaryotic cells, for example to produce hybridoma cells capable of manufacturing monoclonal antibodies in large quantities.

The amount of time required after introduction of the donor oocyte nuclear material to the recipient oocyte for a spindle to integrate may vary from cell type to cell type and/or from species to species. In order to allow sufficient time for the spindle to recover, the hybrid oocyte may require culturing for about one to about twenty minutes, such as about two to about fifteen minutes, such as about five to about ten minutes. In other embodiment, the oocyte can be cultured from about 0.5 hours to about 2.5 hours, from about 1 hour to about 2 hours, from about 1.25 hours to about 2.25 hours, from about 1.5 hours to about 2 hours, from about 1.75 hours to about 2 hours, or about 2 hours after introduction of the donor nucleus to the recipient or host cell.

Formation of Embryos

Following introduction of the donor nuclear genetic material including the chromosomes into the recipient enucleated oocyte the resultant hybrid oocyte can be fertilized in vitro. Protocols for performing in vitro fertilization (IVF) can be found at, for example, U.S. Pat. Nos. 4,589,402, 4,725,579 and in The Handbook of in vitro Fertilization, Eds. Trouson and Gardner, Informa Health Care Publ., 2000, and In vitro Fertilization and Embryo Culture: A Manual of Basic Techniques, Ed. Wolf, Springer Publ., 1988; all incorporated herein by reference in their entireties. There are several issues associated with success in performing IVF. Those issues include, but are not limited to, zona pellucida hardening that leads to decrease in sperm penetration, temperature of fertilization and maintenance of eggs, sperm and embryos, pH, the occurrence of volatile organic compounds found in laboratory air that can harm the process, and other environmental factors.

An exemplary protocol for fertilization includes incubation of hybrid oocytes with the sperm in culture media about 4-12 hours, such as about 5-11 hours, such as about 8 hours. Fertilization is complete with the observation of two pronuclei in the embryo. However, if conventional IVF is not realized, for example due to consequences of oocyte manipulations, a single sperm can be directly injected into the oocyte using intracytoplasmic sperm injections (ICSI). ICSI involves injection of the sperm into the hybrid oocyte, ordinarily through a glass pipette. The methods disclosed herein can include placing sperm in an ICSI medium, capturing the sperm by drawing the medium containing sperm into the pipette, inserting the pipette containing medium and sperm into the hybrid oocyte, and, following insertion into the hybrid oocyte, transferring the medium containing sperm from the pipette into the hybrid oocyte. ICSI methods for use in primates are disclosed in U.S. Patent Publication No. 20030221206, which also discloses "transICSI" methods which result in the production of embryos including heterologous DNA.

The ICSI medium generally includes the constituents water, ionic constituents and a buffer. In some embodiments, the medium lacks phosphate. The buffer used in medium can MOPS or HEPES. Additionally, the ICSI medium may be supplemented with the carbohydrates lactate and pyruvate and the medium may be further supplemented with one or more of the nonessential acids most abundant in the oocyte: glutamine, glycine, proline, serine, and taurine. In one formulation, the ICSI medium used is supplemented with hyaluronate or polyvinylpyrolidone (PVP) to slow or immobilize the sperm so that they may be captured by pipette for the ICSI process.

Exemplary methods are provided in Example 8 below. Human semen sample can be routinely collected following ejaculation. Non-human primate semen samples can be collected by penile electroejaculation (Bavister et al., Biol. Reprod. 28: 983-99, 1983).

In one example, an oocyte from a recipient primate is enucleated using the methods disclosed above, and nuclear material including chromosomes from a donor primate oocyte from the same species is isolated and inserted into the enucleated oocyte. The nuclear donor primate oocyte can be from a subject that has a mitochondrial disorder, while the recipient primate oocyte can be from a subject that does not have the mitochondrial disorder. The donor and the recipient primate oocyte both can be from human, rhesus monkey, or any other mammals, provided both the donor and the recipient are from the same species. The resultant hybrid oocyte is then fertilized using sperm from a male of the same species, and a one-celled embryo is formed. This one celled embryo is totipotent and (i) is capable of four or more cell divisions; (ii) maintains a normal karyotype while in culture; (iii) is capable of differentiating into trophectoderm, germ cells, ectoderm, mesoderm, and endoderm layers; and (iv) comprises mitochondrial DNA derived from the recipient primate oocyte and the chromosomes from the donor primate oocyte of a second primate.

The one celled embryo can be cultured in vitro such that it divides. In some embodiments, the efficiency of producing an 8-celled embryo is greater than about 5%, such as greater than about 10%, greater than about 20%, greater than about 30%, greater than about 40%, greater than about 50%, greater than about 60%, greater than about 70%, greater than about 80% greater than about 90%, or greater than about 95%. In this contact, "about" indicates within 1%.

The one celled embryo can be cultured in vitro, wherein the one celled embryo divides, thereby producing a two-celled, four-celled, eight-celled embryo, a morula or a blastocyst. Methods for culturing embryos are well known in the art, see for example, U.S. Published Patent Application No. 2009/0004740, which is incorporated herein by reference.

Following fertilization, a pregnancy can be established. For example, the one, two, four or eight celled embryo, morula or blastocyst can be introduced into the recipient from which the recipient oocyte was isolated. In one example, the recipient is a primate. In another example, the one, two, four, or eight celled embryo, morula or blastocyst can be introduced a surrogate recipient, such as a primate, of the same species, wherein the surrogate animal is different from the first and the second primate. Generally, the pregnancy is established in an animal of the same species as the oocyte donor.

The embryo can be allowed to develop to term. Methods for the introduction of embryos into a female, and use of surrogate females, in order to produce offspring are well known in the art. In one example, the donor oocyte, recipient oocyte, and surrogate primate are human. However, in other examples, the donor oocyte, recipient oocyte, and surrogate primate are non-human primates, such as rhesus monkeys or macaques. Exemplary protocols are described in Example 8.

Production of Stem Cells

The one celled embryo can also be cultured and used for the production of stem cells. Following fertilization, the resultant embryo is not transplanted into a recipient, but is cultured in vitro. Methods of culturing primate embryos and stem cells are well-known in the art. Any cell culture media that can support the growth and differentiation of human or non-human primate embryonic stem cells can be used. In some embodiments, the pluripotent stem cells are cultured on a feeder layer, such as of murine or primate embryonic fibroblasts. However, the feeder layer can be any cells that support the growth of embryonic stem cells (ESCs). This approach makes for a completely autologous culturing system, thereby eliminating the risk of cross-species contamination. For therapeutic use, the culturing methods can be xeno-free (no xenogeneic cells or components) and additionally avoid the use of serum (such as fetal bovine serum, FBS) in the culturing media.

In some embodiments, non-human or human primate totipotent (TSC) or pluripotent (PSC) stem cells are made using the methods disclosed herein. These stem cells have a variety of uses. TSC or PSC cells readily can be produced from human and non-human primate embryos. In one embodiment, primate TSC or PSC cells are isolated and subsequently cultured in "ES medium," which supports the growth of embryonic stem cells. The PSCs express SSEA-3, SSEA-4, TRA-1-60, and TRA-1-81. For example, ES medium comprises 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), 1% non-essential amino acid stock (Gibco BRL).

In one example, a recipient primate oocyte from a recipient primate is enucleated using the methods disclosed above, and nuclear material including chromosomes from a donor primate oocyte is inserted into the enucleated oocyte, as described herein. The donor oocyte can be from a subject that has a mitochondrial disorder, while the recipient oocyte can be from a subject that does not have the mitochondrial disorder. The donor and the recipient oocyte are from a primate of the same species, such as a human, rhesus monkey, or Japanese macaque monkey. The resultant hybrid oocyte is then fertilized using sperm from a male of the same species, and a one-celled embryo is formed. The resultant cell is then cultured in medium, such as but not limited to protein-free HECM-9 medium and cultured at 37° C. in about 5-6% CO2 until use. These cultures can be maintained under paraffin oil. Once the TSCs reaches about the 2 cell stage or beyond, such as the 4, 8 or 16 cell stage, the cells can be transferred for further culture. In one embodiment, these TSCs are cultured to the blastocyst stage in a culture medium, such as, but not limited to, HECM-9 medium.

In some embodiments, the zonae pellucidae of selected expanded blastocysts are be removed by brief exposure (45-60 seconds) to 0.5% pronase in TH3 medium. In some embodiments an ICM can be isolated from trophectoderm cells by immunosurgery, where zona-free blastocysts are exposed to rabbit anti-rhesus spleen serum for about 30 minutes at abut 37° C. After extensive washing (such as using TH3 medium), embryos are incubated in guinea pig complement reconstituted with HECM-9 (1:2, v/v) for about an additional 30 minutes at about 37°. Partially lysed trophectodermal cells are mechanically dispersed by gentle pipetting, such as with a small bore pipette (for example, about a 125 μm in inner diameter; Stripper pipette, Midatlantic Diagnostics Inc., Marlton, N.J.) followed by the rinsing of ICMs three times, such as with TH3 medium. Isolated ICMs are plated onto a solid substrate, such as onto Nunc 4-well dishes containing mitotically-inactivated feeder layers consisting of mouse embryonic fibroblasts (mEFs) and cultured, such as in DMEM/F12 medium (Invitrogen) with glucose and without sodium pyruvate supplemented with 1% nonessential amino acids (Invitrogen), 2 mM L-glutamine (Invitrogen), 0.1 mM β-mercaptoethanol and 15% FBS and maintained at about 37° C., about 3% $CO_2$, about 5% $O_2$ and about 92% $N_2$ gas conditions. Alternatively, whole, intact blastocysts can be directly plated onto mEFs for ESC isolation. Alternatively, trophectoderm can be removed mechanically, for example using laser-assisted dissection or microscalpel.

After about 1 to about 7 days, cells, such as blastocysts or ICMs that attached to the feeder layer and initiated outgrowth can be dissociated into small cell clumps, such as manual dissociation with a microscalpel, and re-plated onto a new substrate, such as new embryonic fibroblasts (mEFs). After the first passage, colonies with embryonic stem cell (ESC)-like morphology are selected for further propagation, characterization and low temperature storage. Generally, ESC morphology is compact colonies having a high nucleus to cytoplasm ratio, prominent nucleoli, sharp adages and flat colonies. In some examples, the medium is changed daily and ESC colonies are split about every 5-7 days manually or by disaggregation in collagenase IV, (for example, about 1 mg/ml, at about 37° C. for about 2-3 minutes; Invitrogen) and replating collected cells onto dishes with fresh feeder layers. Cultures are maintained at about 37° C., about 3% CO2, about 5% O2 and about 92% N2. In another alternative, serum-free media is used.

PSCs can then be isolated, and PSCs can be maintained in vitro using standard procedures. In one embodiment, primate PSCs are isolated on a confluent layer of fibroblast in the presence of ESC medium. In one example, to produce a feeder layer, xenogeneic embryonic fibroblasts are obtained from 14-16 day old fetuses from outbred mice (such as CF1, available from SASCO), but other strains may be used as an alternative. Alternatively, human fibroblasts obtained from adult skin or cells obtained from TSC-derived fibroblasts can be employed. In another embodiment, tissue culture dishes treated with about 0.1% gelatin (type I; Sigma) can be utilized. Unlike mouse PSC cells, human PSC (hPSC) cells do not express the stage-specific embryonic antigen SSEA-1, but express SSEA-4, which is another glycolipid cell surface antigen recognized by a specific monoclonal antibody (see, for example, Amit et al., *Devel. Biol.* 227:271-278, 2000).

ICM-dissociated cells can be plated on feeder layers in fresh medium, and observed for colony formation. Colonies demonstrating ESC morphology are individually selected, and split again as described above. Resulting PSCs are then routinely split by mechanical methods every six days as the cultures become dense. Early passage cells are also frozen and stored in liquid nitrogen.

PSCs as well as transplantable cells can be produced and can be karyotyped with, for example, a standard G-banding technique (such as by the Cytogenetics Laboratory of the University of Wisconsin State Hygiene Laboratory, which provides routine karyotyping services) and compared to published karyotypes for the primate species.

In other embodiments, immunosurgical isolation of the ICM is not utilized. Thus, the blastocysts are cultured directly, without the use of any immunosurgical techniques. Isolation of primate PSCs from blastocysts, including humans, would follow a similar procedure, except that the rate of development of TSCs to blastocyst can vary by a few days between species, and the rate of development of the cultured ICMs will vary between species. For example, eight days after fertilization, rhesus monkey embryos are at the expanded blastocyst stage, whereas human embryos reach the same stage 5-6 days after fertilization. Because other primates also vary in their developmental rate, the timing of the initial ICM split varies between primate species, but the same techniques and culture conditions will allow ESC isolation (see U.S. Pat. No. 6,200,806, which is incorporated herein by reference for a complete discussion of primate ES cells and their production). Culture conditions described above can also be used for the culture of PSCs from blastocysts.

Conditions for culturing human TSCs obtained by conventional protocols from fertilized oocyte to the blastocyst have been described (see Bongso et al., *Hum Reprod.* 4:706-713, 1989). In some embodiments, co-culturing of human TSCs with human oviductal cells results in the production of high quality blastocyst. Human ICM from blastocysts grown in cellular co-culture, or in media that eliminates the feeder cell layer requirement, allows isolation of human PSCs with the same procedures described above for non-human primates.

Pluripotent stem cells can also be produced using the methods described herein. The TSC can then be cultured as described above to produce PSCS and multipotent stem cells (MPSCs). A therapeutically effective amount of the mulitpotent cells can then be utilized in the subject of interest. In one embodiment, cells matched at one or more MHC loci to the treated individual. In a one embodiment, the cells are cultured in media free of serum. In another another embodiment, the cells have not been cultured with xenogeneic cells (e.g., non-human fibroblasts such as mouse embryonic fibroblasts). Methods for treating disease are provided that comprise transplanting cells derived from PSCs in a primate afflicted with a disease characterized by damaged or degenerative somatic cells. Such cells can be multipotent cells or any other type of tranplantable cells.

The primate PSCs described herein are useful for the generation of cells of desired cell types. In some embodiments, the PSCs are used to derive mesenchymal, neural, and/or hematopoietic stem cells. In other embodiments, the PSCs are used to generate cells, including but not limited to, pancreatic, liver, bone, epithelial, endothelial, tendons, cartilage, and muscle cells, and their progenitor cells. Thus, transplantable cells derived from PSCs can be administered to an individual in need of one or more cell types to treat a disease, disorder, or condition. Examples of diseases, disorders, or conditions that may be treated or prevented include neurological, endocrine, structural, skeletal, vascular, urinary, digestive, integumentary, blood, immune, autoimmune, inflammatory, kidney, bladder, cardiovascular, cancer, circulatory, hematopoietic, metabolic, reproductive and muscular diseases, disorders and conditions. In some embodiments, a hematopoietic stem cell derived from primate PSCs is used to treat cancer. In some embodiments, these cells are used for reconstructive applications, such as for repairing or replacing tissues or organs.

The TSCs and PSCs described herein can be used to generate multipotent stem cells or transplantable cells. In one example, the transplantable cells are mesenchymal stem cells. Mesenchymal stem cells give rise to a very large number of distinct tissues (Caplan, *J. Orth. Res* 641-650, 1991). Mesenchymal stem cells capable of differentiating into bone, muscles, tendons, adipose tissue, stromal cells and cartilage have also been isolated from marrow (Caplan, *J. Orth. Res.* 641-650, 1991). U.S. Pat. No. 5,226,914 describes an exemplary method for isolating mesenchymal stem cells from bone marrow. In other examples, epithelial progenitor cells or keratinocytes can be generated for use in treating conditions of the skin and the lining of the gut (Rheinwald, *Meth. Cell Bio.* 21A:229, 1980). The cells can also be used to produce liver precursor cells (see PCT Publication No. WO 94/08598) or kidney precursor cells (see Karp et al., *Dev. Biol.* 91:5286-5290, 1994). The cells can also be used to produce inner ear precursor cells (see Li et al., *TRENDS Mol. Med.* 10: 309, 2004).

The transplantable cells can also be neuronal cells. The volume of a cell suspension, such as a neuronal cell suspension, administered to a subject will vary depending on the site of implantation, treatment goal and amount of cells in solution. Typically the amount of cells administered to a subject will be a therapeutically effective amount. For example, where the treatment is for Parkinson's disease, transplantation of a therapeutically effective amount of cells will typically produce a reduction in the amount and/or severity of the symptoms associated with that disorder, e.g., rigidity, akinesia and gait disorder. In one example, a severe Parkinson's patient needs at least about 100,000 surviving dopamine cells per grafted site to have a substantial beneficial effect from the transplantation. As cell survival is low in brain tissue transplantation in general (5-10%) at least 1 million cells are administered, such as from about 1 million to about 4 million dopaminergic neurons are transplanted. In one embodiment, the cells are administered to the subject's brain. The cells can be implanted within the parenchyma of the brain, in the space containing cerebrospinal fluids, such as the sub-arachnoid space or ventricles, or extaneurally. Thus, in one example, the cells are transplanted to regions of the subject which are not within the central nervous system or peripheral nervous system, such as the celiac ganglion or sciatic nerve. In another embodiment, the cells are transplanted into the central nervous system, which includes all structures within the dura mater. Injections of neuronal cells can generally be made with a sterilized syringe having an 18-21 gauge needle. Although the exact size needle will depend on the species being treated, the needle should not be bigger than 1 mm diameter in any species. Those of skill in the art are familiar with techniques for administering cells to the brain of a subject.

Generally a therapeutically effective amount of cells is administered to an individual. The cells can be administered in a pharmaceutical carrier. The pharmaceutically acceptable carriers of use are conventional. For example, *Remington's Pharmaceutical Sciences*, by E. W. Martin, Mack Publishing Co., Easton, Pa., 15th Edition (1975), describes compositions and formulations suitable for pharmaceutical delivery of the cells herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The individual can be any subject of interest. Suitable subjects include those subjects that would benefit from proliferation of cells derived from stem cells or precursor cells. In one embodiment, the individual is in need of proliferation of neuronal precursor cells and/or glial precursor cells. For example, the individual can have a neurodegenerative disorder or have had an ischemic event, such as a stroke. Specific, non-limiting examples of a neurodegenerative disorder are Alzheimer's disease, Pantothenate kinase associated neurodegeneration, Parkinson's disease, Huntington's disease (Dexter et al., *Brain* 114:1953-1975, 1991), HIV encephalopathy (Miszkziel et al., *Magnetic Res. Imag.* 15:1113-1119, 1997), and amyotrophic lateral sclerosis. Suitable individual also include those subjects that are aged, such as individuals who are at least about 65, at least about 70, at least about 75, at least about 80 or at least about 85 years of age. In additional examples, the individual can have a spinal cord injury, Batten's disease or spina bifida. In further examples, the individual can have hearing loss, such as a subject who is deaf, or can be in need of the proliferation of stem cells from the inner ear to prevent hearing loss.

TSCs can also be used to generate extraembryonic cells, such as trophectoderm, that are of use in cell culture. In one embodiment, the use of autologous cells (e.g., trophectoderm) as feeder cells can be helpful to generate stem cells that in turn have the capacity to differentiate into differentiated organ-specific cells. In other embodiments, the use of allogeneic feeder cells, obtained by using culturing totipotent stem cells in such a manner to allow the generation of such feeder layer component, is useful to avoid xeno-contamination and thus, allow for easier FDA approval of the differentiated cells cultured thereupon for therapeutic purposes.

Cells produced by the methods disclosed herein, such as TSC and PSC are also of use for testing agents of interest, such as to determine if an agent affects differentiation or cell proliferation. For example, TSCs or PSCs are contacted with the agent, and the ability of the cells to differentiate or proliferate is assessed in the presence and the absence of the agent. Thus, cells produced by the methods disclosed herein can also be used in to screen pharmaceutical agents to select for agents that affect specific human cell types, such as agents that affect neuronal cells. Cell produced by the methods disclosed herein can also be used to screen agent to select those that affect differentiation. The test compound can be any compound of interest, including chemical compounds, small molecules, polypeptides or other biological agents (for example antibodies or cytokines). In several examples, a panel of potential agents are screened, such as a panel of cytokines or growth factors is screened.

Methods for preparing a combinatorial library of molecules that can be tested for a desired activity are well known in the art and include, for example, methods of making a phage display library of peptides, which can be constrained peptides (see, for example, U.S. Pat. No. 5,622, 699; U.S. Pat. No. 5,206,347; Scott and Smith, *Science* 249:386-390, 1992; Markland et al., *Gene* 109:13-19, 1991), a peptide library (U.S. Pat. No. 5,264,563); a peptidomimetic library (Blondelle et al., *Trends Anal Chem.* 14:83-92, 1995); a nucleic acid library (O'Connell et al., *Proc. Natl Acad. Sci., USA* 93:5883-5887, 1996; Tuerk and Gold, *Science* 249:505-510, 1990; Gold et al., *Ann. Rev. Biochem.* 64:763-797, 1995); an oligosaccharide library (York et al., *Carb. Res.* 285:99-128, 1996; Liang et al., *Science* 274: 1520-1522, 1996; Ding et al., *Adv. Expt. Med. Biol.* 376: 261-269, 1995); a lipoprotein library (de Kruif et al., *FEBS Lett.* 3 99:23 2-23 6, 1996); a glycoprotein or glycolipid library (Karaoglu et al., *J Cell Biol.* 130.567-577, 1995); or a chemical library containing, for example, drugs or other pharmaceutical agents (Gordon et al., *J Med. Chem.* 37.1385-1401, 1994; Ecker and Crooke, *BioTechnology* 13:351-360, 1995). Polynucleotides can be particularly useful as agents that can alter a function pluripotent or totipotent cells because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, TSCs, PSCs or MPSCs produced by the methods disclosed herein can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the cells, particularly with respect to the function being examined. An advantage of using a high throughput format is that a number of test agents can be examined in parallel, and, if desired, control reactions also can be run under identical conditions as the test conditions. As such, the methods disclosed herein provide a means to screen one, a few, or a large number of test agents in order to identify an agent that can alter a function of the cells, for example, an agent that induces the cells to differentiate into a desired cell type, or that prevents spontaneous differentiation, for example, by maintaining a high level of expression of regulatory molecules.

The cells are contacted with test compounds sufficient for the compound to interact with the cell. When the compound binds a discrete receptor, the cells are contacted for a sufficient time for the agent to bind its receptor. In some embodiments, the cells are incubated with the test compound for an amount of time sufficient to affect phosphorylation of a substrate. In some embodiments, cells are treated in vitro with test compounds at 37° C. in a 5% $CO_2$ humidified atmosphere. Following treatment with test compounds, cells are washed with $Ca^{2+}$ and $Mg^{2+}$ free PBS and total protein is extracted as described (Haldar et al., *Cell Death Diff* 1:109-115, 1994; Haldar et al., *Nature* 342:195-198, 1989; Haldar et al., *Cancer Res.* 54:2095-2097, 1994). In additional embodiments, serial dilutions of test compound are used.

The disclosure is illustrated by the following non-limiting Examples.

EXAMPLES

Example 1

Methods

Ovarian Stimulation, Recovery of Rhesus Macaque Oocytes, Fertilization and Embryo Culture:

Controlled ovarian stimulation and oocyte recovery are routine in our laboratory and have been described previously (Zelinski-Wooten et al., Hum Reprod, 1995. 10(7): p. 1658-66). Cycling females were subjected to follicular stimulation using twice-daily intramuscular injections of recombinant human FSH as well as concurrent treatment with Antide, a GnRH antagonist, for 8-9 days. Females received recombinant human LH on days 7-9 and recombinant HCG on day 10. Cumulus-oocyte complexes were collected from anesthetized animals by laparoscopic follicular aspiration (28-29 hrs post hCG) and placed in Hepes-buffered TALP containing 0.3% BSA (TH3) at 37° C. Oocytes, stripped of cumulus cells by mechanical pipetting after brief exposure (<1 min) to hyaluronidase (0.5 mg/ml), were placed in chemically defined, protein-free HECM-9 medium (McKiernan and Bavister, Hum Reprod, 2000. 15(1): p. 157-64) at 37° C. in 5% $CO_2$, 5% $O_2$ and 90% $N_2$ until further use. For ISCI, sperm was diluted with 10% polyvinylpyrrolidone (1:4) and a 5 µl drop was placed in a micromanipulation chamber. A 30 µl drop of TH3 was placed in the same micromanipulation chamber next to the sperm droplet and both were covered with paraffin oil. The micromanipulation chamber was mounted on an inverted microscope equipped with Hoffman optics and micromanipulators. An individual sperm was immobilized, aspirated into an ICSI pipette and injected into the cytoplasm of a MII oocyte, away from the polar body. After fertilization, embryos were placed in 4-well dishes containing HECM-9 medium and cultured at 37° C. in 5% $CO_2$, 5% $O_2$ and 90% $N_2$. Embryos at the 8-16 cell stage were transferred to fresh plates of HECM-9 medium supplemented with 5% FBS and cultured to the blastocyst stage (usually on days 7-8) with medium change every other day. During the culture period, embryos were periodically scored based on morphological criteria.

Oocyte Freezing:

Vitrification of freshly retrieved mature oocytes was done by first exposing the oocytes to a solution of 7.5% dimethylsulfoxide (DMSO) plus 7.5% ethylene glycol (EG) in HEPES-buffered TALP medium containing 20% fetal bovine serum ($TH_2O$) for 3 minutes before transfer to a solution of 15% DMSO, 15% EG, and 0.5 M sucrose in $TH_2O$. During the last step, oocytes were loaded into Cryo-Tips (Irving Scientific) and heat-sealed within 90 sec, then plunged into liquid nitrogen. Subsequent warming and cryoprotectant removal was done by a 3 second thaw in a 37° C. water bath, cutting the tip and expelling the oocytes into 1 M sucrose for 2 min, 0.5 M sucrose for 4 minutes, and $TH_2O$ for 6 min before transfer into culture media. All manipulation procedures were done at room temperature.

Embryo Transfer:

Adult, multiparous females were used as recipients and monitored for menses. Daily blood samples were collected beginning on day 8 of the menstrual cycle and serum levels of estradiol will be quantitated by RIA. The day following the peak in serum estradiol will be considered the day of ovulation (day 0). Within 0 to 5 days of ovulation, recipient females were anesthetized with isoflurane gas vaporized in 100% oxygen and followed by comprehensive physiologic monitoring throughout the surgery, including electrocardiogram, peripheral oxygen saturation, and end-expired carbon dioxide. Orotracheal intubation and mechanical ventilation to maintain expired $CO_2$ at less than 50 mm Hg were mandatory. After sterile skin preparation and draping, the abdomen was insufflated with $CO_2$ at 15 mm Hg pressure and the viewing telescope was inserted via a small supraumbilical incision, with accessory ports placed in the paralumbar region. The monkey was placed in the Trendeleburg position, allowing the viscera to migrate in a cephalad direction, exposing the reproductive organs. After insertion of the telescope, the ovaries were examined with a self-retaining microretractor inserted at a high paramedian position. The transfer was conducted into the oviduct with an ovulation site on the associated ovary. The fimbria was grasped with a Patton retractor and placed in traction. The guide cannula was introduced into the oviduct. Typically, two ICSI embryos were transferred. Embryos were removed from culture medium and transferred to a dish containing TH3 medium. The Patton polyurethane transfer catheter connected to a 1-ml syringe was filled with 0.01-0.02 ml of TH3 medium, avoiding air bubbles. Embryos were carefully loaded near the catheter tip with a total volume not exceeding 0.03 ml. The catheter was then inserted transabdominally and advanced through the fimbrium into the oviduct for a distance of 1-3 cm, where the embryos were deposited. Following transfer, the catheter was removed and carefully examined and rinsed to ensure that all embryos were expelled. In the event of a retained embryo, a second transfer was attempted. As alternative, embryos were placed at minilaparotomy into the oviducts of recipients (Mitalipov et al, Biol Reprod, 2002. 66(5): p. 1367-73).

Following embryos transfer, the insufflation was reduced and the incisions were closed with interrupted absorbable suture in an intradermal pattern. Postoperative analgesia was provided through administration of buprenorphine (0.03 mg/kg, 1 M).

Immunocytochemical Procedures:

ICC of primate oocytes embryos and ES cells was routinely performed. Oocytes and embryos were fixed in 4% paraformaldehyde for 20 min. ES cells were plated onto glass culture (chamber) slides pre-coated with gelatin or polyornithine/laminin before fixation in 4% paraformaldehyde. After rinsing 3 times with PBS, oocytes, embryos and cells were permeabilized with 0.2% Triton X-100 and 0.1% Tween-20 in PBS for 40 minutes at room temperature. Cells were then incubated with 2% normal serum for 30 minutes at room temperature, and after extensive washing, incubated with primary antibodies diluted to the optimal concentration (usually 1:200) with 0.05% Tween-20 for 40 min at room temperature. After rinsing (same as above), cells were incubated with fluorophore-tagged secondary antibodies (diluted in the same solution as primary antibodies) for 40 minutes in the dark at room temperature followed by washing and counterstaining with DAPI for 10 min. Oocytes and embryos were transferred into 10 ul drop of mounting medium and covered with coverslip glasses. The slides containing cells were also covered with coverslips. Specimens are examined under epifluorescence or confocal microscopy and mages of identified phenotypes can be captured either by a Nikon fluorescence microscope with CCD camera, or by confocal microscopy.

Cytogenetic Analysis:

Mitotically active ES cells in log phase were incubated with 120 ng/mL ethidium bromide for 40 min at 37° C., 5% $CO_2$, followed by 120 ng/ml colcemid treatment for 20-40 min. Cells will be dislodged with 0.25% trypsin, and centrifuged at 200×g for 8 min. The cell pellet was gently resuspended in 0.075 M KCl solution and incubated for 20 min at 37° C. followed by fixation with methanol:glacial acetic acid (3:1) solution. Fixed cells were dropped on wet slides, air dried and baked at 90° C. for 1 hour. G-banding was performed using trypsin-EDTA and Leishman stain (GTL) by immersing slides in 1× trypsin-EDTA with 2 drops of 0.4M $Na_2HPO_4$ for 20 to 30 seconds. Slides were rinsed in distilled water and stained with Lieschman Stain for 1.5 minutes, rinsed in distilled water again, and air dried. For GTL-banding analysis, 20 metaphases were fully karyotyped under an Olympus BX40 microscope equipped with 10× and 100× plan-Apo objectives. Images were then captured and chromosomes analyzed using a CYTOVISION® digital imaging system.

Karyotype analysis of blastocysts produced by ST was carried out using fluorescent in situ hybridization (FISH). Embryos will be individually fixed and FISH will be performed using probes specific for five macaque chromosomes X, Y, 17, 18, and 20 (homologous to human chromosomes X, Y, 13, 18, and 16, respectively) following previously published protocols (Dupont et al., Chromosomal instability in rhesus macaque preimplantation embryos. Feral Steril, 2008).

Mitochondrial DNA Analysis:

mtDNA was extracted from the blood using Genomic DNA Purification Kit (Gentra systems, Minnesota, USA). The rhesus macaque mitochondrial D-loop hypervariable region 2 informative domain 1 (rhDHV2 ID) sequence was amplified for each sample using primers RhDF2 (5'-TAACATATCCGATCAGAGCC-3') (SEQ ID NO: 1) and RhDR (5'-TTAAACACCCTCTACGCCG-3') (SEQ ID NO: 2). PCR product at expected size of 544 bp was then sequenced to determine unique SNPs. Real-time PCR primers and fluorescent probes (TaqMan MGB probe; Applied Biosystems, USA) corresponding to each unique SNP will be designed for qPCR analysis. Each RhHDV2 PCR fragments then will be subcloned in PCR2.1 vector (Invitrogen, CA USA) and serial dilutions for each mtDNA type were prepared at the ratio 0; 0, 5, 1, 5, 10, 20, 30, 40, 50, 60, 70, 80, 90, 100%. QPCR reactions will be repeated ten times, and the average value will be applied for standard curves.

Example 2

Spindle Transfer in Monkey MII Oocytes

Initially, the distribution of active mitochondria in monkey oocytes and early embryos was investigated by labeling with MITOTRACKER™ Red staining and confocal laser scanning microscopy. In GV stage oocytes, accumulation of mitochondria in the peripheral cytoplasm and in the perinuclear area around the germinal vesicles was observed. Similar distribution of active mitochondria was detected in pronuclear stage zygotes. In contrast, in mature metaphase II (MII)-stage oocytes mitochondria were distributed relatively even throughout the cytoplasm, and spindles and metaphase chromosomes were free of mitochondria (FIG. 2A-C). These results suggest that isolation and transfer of MII spindles will not result in a significant mtDNA carry over from the nuclear donor oocyte.

A noninvasive MII oocyte enucleation procedure using a computer controlled spindle imaging system was one of the key improvements that allowed significant improvement for monkey SCNT protocols and succeed in the reprogramming of adult somatic cells to the pluripotent state. The modified enucleation technique was applicable to the isolation of intact MII spindles and their subsequent transfer to enucleated cytoplasts. Mature MII oocytes were transferred to the micromanipulation chamber in 30 µl of TH3 containing 5 µg/ml cytochalasin B, and incubated for 10-15 min before enucleation. The chamber was then mounted on an inverted microscope equipped with Relief contrast optics and micromanipulators. The metaphase spindle was visualized using an OOSIGHT™ Imaging System that allowed non-invasive, polarized light imaging and detection of the spindle based on birefringence. An individual oocyte was positioned using the holding pipette with the spindle at approximately 12 to 3 o'clock (FIG. 2D). A small gap in the zona pellucid was punctured using a laser pulse. A beveled (20-22 µm outer diameter) enucleation pipette was inserted through the zona pellucida opening without piercing the oolemma and the spindle with surrounding cytoplasm (karyoplast) was slowly aspirated into the pipette and removed. The karyoplast was then slowly expelled from the pipette into a micro drop (FIG. 2E). Karyoplasts were isolated with intact spindles with 100% efficiency. We measured diameters of both karyoplasts and cytoplasts (FIG. 2E) and calculated that an average volume of a karyoplast was 11.33±1.23 pL (mean±SEM) while the average volume of a cytoplast was 752.05±18.3 pL. Thus, a karyoplast contained approximately 1.5% of the volume of a cytoplast.

Next, karyoplasts were placed into the perivitelline space of cytoplasts, on the side opposite the $1^{st}$ polar body and transferred to the fusion chamber (FIG. 2F). Fusion of couplets was induced by electroporation using standard protocols consisting of two 50 µsec DC pulses of 2.7 kV/cm in 0.25 M D-sorbitol buffer containing 0.1 mM calcium acetate, 0.5 mM magnesium acetate, 0.5 mM HEPES and 1 mg/ml fatty acid-free BSA. Approximately 1 hour after fusion, reconstructed oocytes were fixed and analyzed by immunocytochemistry (ICC) for spindle integrity. The majority of ST oocytes resumed meiotic division and progressed to the anaphase of meiosis II or had completed meiosis and separated the $2^{nd}$ polar body prior to fertilization (FIG. 2G).

It was possible that fusion by electroporation triggered premature activation and subsequent resumption of meiosis. To test this hypothesis, an alternative karyoplast fusion technique was employed using a commercially available extract from Sendai virus (SeV). Isolated karyoplasts were briefly exposed to the SeV extract and placed into the perivitelline space of cytoplasts opposite to the $1^{st}$ polar body. Fusion occurred within 20-30 min. Analysis of reconstructed oocytes created using SeV fusion demonstrated that spindles were maintained in the MII stage and had normal morphology similar to intact controls (FIG. 2H). Resumption of meiosis and separation of the $2^{nd}$ polar body was observed in SeV group only after fertilization by ISCI (FIG. 3A-D). Thus, these results indicate that electrofusion pulse induces premature activation and resumption of meiosis during spindle introduction. In contrast, this side effect was circumvented by using SeV-assisted fusion.

In the next set of experiments, the developmental competence of ST oocytes produced by electrofusion or SeV following fertilization by ISCI and in vitro embryo culture was determined. Pronuclear formation (fertilization) and cleavage rates in the SeV group were similar to the control (Table 1). Pronuclear formation in electrofusion group was not observed and all oocytes in this group prematurely cleaved by the next day morning after fertilization.

TABLE 1

Fertilization and embryo development after spindle transfer

| Treatment | # Oocytes | # Lysed | # Pronuclei (%) | # Cleaved (%) | # 8-cell (%)* | # Morulae (%)* | # Compact Morulae (%)* | # Blastocysts (%)* |
|---|---|---|---|---|---|---|---|---|
| Electrofusion | 11 | 4 | 0 | 7 (100) | 4 (57) | 1 (14) | 1 (14) | 0 (0) |
| SeV | 22 | 1 | 19 (90) | 19 (100) | 18 (95) | 16 (84) | 16 (84) | 16 (84) |

TABLE 1-continued

Fertilization and embryo development after spindle transfer

| Treatment | # Oocytes | # Lysed | # Pronuclei (%) | # Cleaved (%) | # 8-cell (%)* | # Morulae (%)* | # Compact Morulae (%)* | # Blastocysts (%)* |
|---|---|---|---|---|---|---|---|---|
| ICSI control | 10 | 0 | 10 (100) | 10 (100) | 9 (90) | 9 (90) | 9 (90) | 7 (70) |

*Percentages are calculated based on the number of cleaved embryos

Figure 3A:
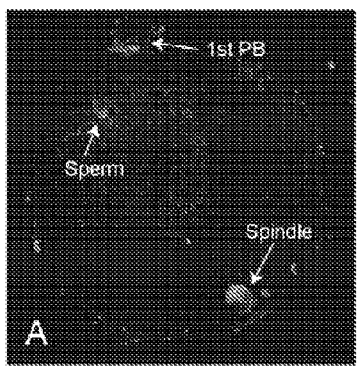
FIGS. 3A-3E are a set of digital images showing fertilization and embryo development following ST. A, resumption of meiosis and progression to the anaphase II in Sendai virus extract (SeV) group 1 hour after fertilization. B, C, the same image as in A with the magnified spindle. D, segregation of the 2$^{nd}$ polar body and pronuclear formation in SeV group. E, blastocyst stage embryos produced from ST oocytes.
Figure 3B:
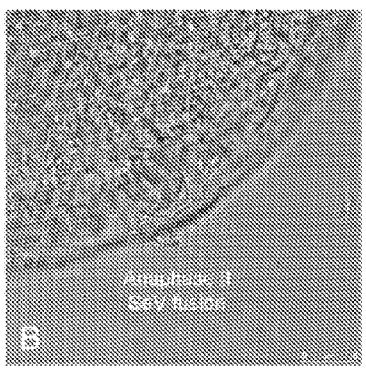
Figure 3C:
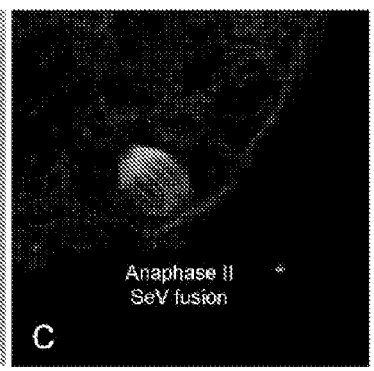
Figure 3D:
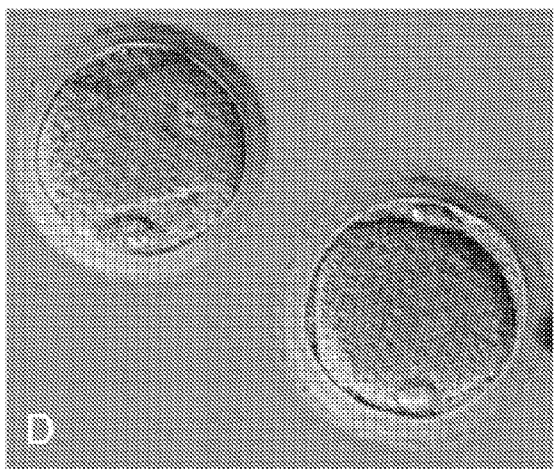
Figure 3E:
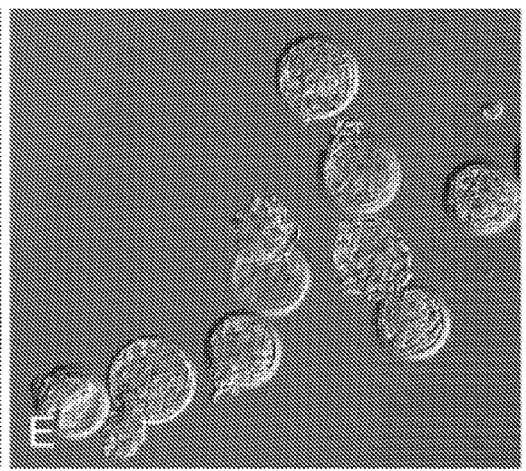
Figure 4:
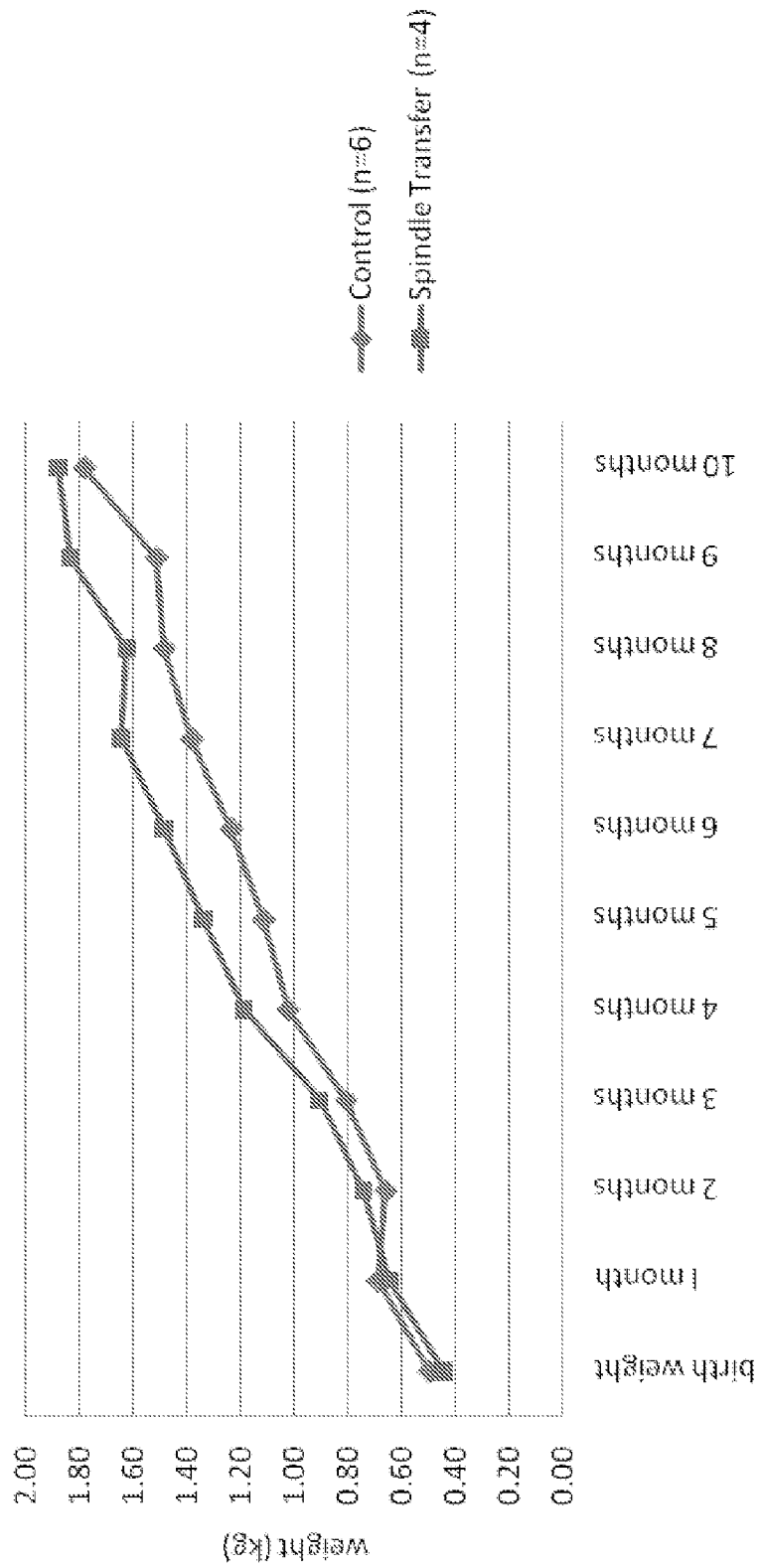
FIG. 4 is a graph of the average growth rate of experimentally produced infants in comparison to controls.

However, all embryos in this group arrested beyond the 8-cell stage, while the majority of embryos in the SeV exposed and intact control groups progressed to blastocysts (FIG. 3E).

Example 3

Production of Rhesus Monkey ES Cells and Pregnancies by Spindle Transfer

Fifteen blastocysts produced from reconstructed oocytes were selected and used for the derivation of ES cells. The inner cell mass (ICM) was isolated by laser-assisted selective dispersal of trophectodermal cells and plated onto feeder layers consisting of mouse embryonic fibroblasts (mEFs) [34, 37]. After 5-7 days of culture, ICMs and intact blastocysts that attached to the feeder layer and initiated three dimensional outgrowths were manually dissociated into smaller clumps and replated onto fresh feeder layers. Subsequent passaging gave rise to three ES cell lines. Detailed parentage analysis of nuclear DNA employing 40 microsatellite markers revealed that the nuclear material was from the spindle donor monkey. While mtDNA analysis conducted by direct sequencing of the D-loop region clearly confirmed that mtDNA in ES cells originated from the cytoplast donor [34, 38]. Based on the sequence analysis of 16 informative single nucleotide polymorphisms (SNPs) between the two females, no contribution of the mtDNA by the spindle donor was detected. Karyotype and quantitative mtDNA analysis for a possible heteroplasmy in these ES cell lines is currently ongoing. More recently, seven embryo transfers involving 13 ST embryos generated by SeV were conducted. Three recipients become pregnant, one carrying twins and two singletons (a 29% pregnancy rate). Fetal measurements and heart rates was determined by ultrasonography at 8 weeks of pregnancy were within normal ranges for this stage of development.

Overall, these results demonstrate, for the first time, that MII spindles can be isolated and transplanted into enucleated oocytes with high efficiently. Reconstructed oocytes were suitable for fertilization and developed to blastocysts at rates similar to controls. Moreover, isolation of ES cells and the establishment of three ongoing pregnancies demonstrates the feasibility and high efficiency of ST as a new reproductive technology for mtDNA replacement.

Example 4 mtDNA Replacement Approaches in Rhesus Monkey Oocytes

Unfertilized mature MII-arrested oocytes are the most optimal stage for mtDNA replacements due to their even cytoplasmic distribution of mitochondria as opposed to nucleated oocytes and embryos. Several studies have indicated that mitochondria in mature human oocytes are evenly dispersed in the ooplasm, while after fertilization they appeared to migrate and concentrate around zygotic pronuclei [26, 36, 39]. The studies described above on mitochondrial staining in monkey oocytes and zygotes also support this observation. These observations allow the isolation and transfer of nuclear material with a minimum amount of mitochondria resulting in the least degree of heteroplasmy in reconstructed oocytes.

It was determined that MII spindles can be visualized and extracted as karyoplasts under polarized microscopy without damage to the spindle. However, spindle introduction into the cytoplast was a critical step. Premature resumption of meiosis was observed when fusion was induced by electroporation. In contrast, fusion with a SeV extract did not cause premature activation and spindle integrity was retained in reconstructed oocytes. The extract is inactivated and purified from the genomic RNA of the SeV and does not have any infective or proliferative potentials. However, it can be beneficial to use polyethyleneglycol (PEG) or modified electrofusion. Electroporation of oocytes in $Ca^{2+}$-containing fusion medium resulted in increased intracellular calcium levels which, in turn, trigger premature oocyte activation and resumption of meiosis. The exclusion of $Ca^{2+}$ from the electrofusion buffer overcomes this undesirable side effect. PEG-assisted fusion also will not induce activation and affect spindle integrity and allows efficient karyoplast/cytoplast fusion.

For each experiment, oocytes are collected from two unrelated females following controlled ovarian stimulations (see Example 1) and enucleated. After all oocytes are enucleated, karyoplasts from the first female are fused with cytoplasts from the second monkey and vice versa. Two experimental fusion techniques are utilized, PEG and modified electroporation. Fusion with SeV extract and intact oocytes will be used as a control.

For PEG, a karyoplast is aspirated into a micropipette, transferred into a micro drop containing 50% PEG solution and are briefly exposed to the solution by pipetting in and out several times, as described above. Next, the karyoplast is placed into the perivitelline space of the cytoplast on the side opposite the 1st polar body. For electroporation, cell fusion is induced by two 50 μsec DC pulses of 2.7 kV/cm in modified D-sorbitol buffer without $Ca^{2+}$. Successful fusion is confirmed visually 30 min after the transfer by the disappearance of the karyoplast in the perivitelline space. Approximately 1-2 hours after ST, fertilization by ISCI and subsequent embryo culture using the methods described in Example 1.

Lysis, fusion rates, fertilization and embryo development are compared between different ST treatments and intact controls. For each treatment, reconstructed oocytes are also fixed before and after ISCI and labeled with monoclonal antibody against spindle proteins, α and β tubulins, costained with 2 μg/ml of 4',6-diamidino-2-phenylindole (DAPI) for 10 min, whole-mounted onto slides and examined under epifluorescence microscopy. Spindle morphology is evaluated based on microtubule organization and chromosome distribution as described previously [40, 41]. Remaining reconstructed embryos are cultured to blastocysts in HECM-9 medium and harvested blastocysts are analyzed by immunocytochemistry (ICC) for OCT4 or NANOG to determine cell counts in the inner cell mass (ICM) and trophectoderm (TE) as described in Example 1.

In addition, a portion of produced blastocysts are used for the karyotype and mtDNA analyses to determine the ploidy and heteroplasmy of reconstructed embryos. Karyotype analysis is carried out using fluorescent in situ hybridization (FISH) with rhesus specific probes for chromosomes X, Y, 17, 18, and 20 following previously published protocols [42]. MtDNA heteroplasmy is determined based on the presence of SNPs in the D-loop region. This is a highly polymorphic region in the rhesus macaque mtDNA with multiple SNPs, unique for each unrelated animal. For example, two egg donor females that were used for ST and isolation of an ES cell line in Preliminary Studies had 16 different mtDNA SNPs. Primers and probes are used for quantitative real-time PCR to estimate the relative presence of each mtDNA type.

Fusion following electroporation occurs at the same rate as seen with SeV extract exposure. However, the use of a modified buffer precludes the problem of premature oocyte activation and the resultant alteration of intact spindles. Such reconstructed oocytes support normal fertilization and high blastocyst developmental rates similar to those observed with SeV treatment.

PEG is suitable for ST but must be used at low concentrations due to toxicity.

Example 5

Use of Cryopreserved Oocytes

The low temperature storage of human oocytes is an important adjunct to clinical IVF programs providing a unique opportunity for preserving the reproductive potential of young cancer patients undergoing chemotherapy or radiation therapy and for couples involved in routine IVF treatment when complications (e.g. inadequate semen quality) arise unexpectedly. The last few years have seen a significant resurgence of interest in the potential benefits of human egg freezing in the context of generating donor "egg banks" to facilitate and lessen the cost of oocyte donation for women that are unable to produce their own oocytes. Current technology requires that the oocyte donor and recipient undergo synchronous ovarian stimulation protocols.

Oocyte cryopreservation outcomes using slow rate cooling protocols have been less effective that those with fertilized embryos. However, the vitrification of human oocytes during IVF cycles has recently been greatly improved resulting in high survival rates and pregnancies [43, 44]. Here, a vitrification protocol is adopted to rhesus monkey oocytes using a commercially available kit with evaluation of its potential for ST. Mature MII oocytes will be first analyzed for spindle morphology using an "Oosight" live imaging system. Vitrification will be performed by quickly transferring oocytes through high concentrations of cryoprotectants (15% v/v DMSO, 15% v/v ethylene glycol, 0.5 mol/l sucrose) followed by loading into CryoTips (FREEZE-AND-THAW™ vitrification kit from Irvine Scientific) and plunging directly into liquid nitrogen. Thawing is conducted, approximately 1 week later, following standard manufacturer protocols and survival of oocytes is assessed first by morphological evaluation under inverted microscopy and by OOSIGHT™ software for spindle morphology at 1 hour and 4 hours post thaw with culture between observations in HECM-9 medium. Upon second imaging, oocytes are enucleated and fused with karyoplasts isolated from fresh oocytes. Additionally, karyoplasts from frozen/thawed oocytes are fused with fresh cytoplasts. Alternatively, both karyoplasts and cytoplasts are prepared from frozen/thawed oocytes. ST can be performed by any method described above. Oocytes are fertilized by ISCI and cultured to blastocysts as outlined above. A portion of ST oocytes are used prior to and post fertilization for the analysis of spindle morphology and meiotic progression by ICC as described above. Intact frozen/thawed and fresh oocytes are used as controls. Fertilized ST oocytes are cultured in HECM-9 medium for up to 8 days and harvested blastocysts are used to determine cell counts as well as for karyotype and mtDNA analyses.

High survival rates are achieved after freeze/thawing oocytes with blastocyst development after ST similar to fresh controls. ES cell lines are derived and pregnancies are produced from cryopreserved ST oocytes.

Example 6

ES Cells from Reconstructed Blastocysts mtDNA Heteroplasmy

Blastocysts are generated using as described herein. ES cells are derived following follow standard protocols well established in our laboratory. Initially, all newly established cell lines are subjected to detailed expression analysis for a unique set of surface markers and transcription factors associated with pluripotency using immunolabeling with specific antibodies against SSEA-3/4, TRA-1-60/81, OCT4 and alkaline phosphatase [37]. Next, all cell lines are subjected to detailed parentage analysis by genetic testing. Genetic testing of nuclear DNA is performed using microsatellite (short tandem repeat) analysis. A combination of 44 microsatellites are sued to determine specific individual rhesus macaque pedigrees [46]. In parallel, mtDNA sequence analysis is performed [34] to prove that in ST-derived ES cells, mitochondria are mainly inherited from cytoplast donors. In addition, a sensitive quantitative mtDNA analysis is employed to determine mtDNA heteroplasmy and the relative amount of each mtDNA variant. This is performed using qPCR assay based on sequence differences in the hyper variable D-loop region as described above. Karyotypic integrity of all established cells is analyzed by detailed G-banding and FISH approaches and cytogeneitics.

As mentioned above, each cell line is subjected to defined in vitro differentiation protocols into two specific cell types—neurons and cardiomyocytes. The rationale is to investigate possible mtDNA segregation in heteroplasmic ES cell lines upon their directed differentiation. One of the first steps in induced in vitro differentiation involves the formation of embryoid bodies (EBs), so called because of their morphological similarity to blastocyst stage embryos. EB production is induced by suspension culture in the absence of feeder layers. To induce cardiac differentiation, 7-10 day old EBs are plated into collagen-coated dishes for further adhesion culture in ES cell medium for an additional 2-3 weeks. Clusters of spontaneously contracting cardiomyocytes are collected and analyzed for mtDNA as described above. Alternative protocols for directed differentiation into cardiomyocytes using DMSO or 5-aza-2-deoxycytodine are available in the art.

Neuronal differentiation is induced by step-wise directed differentiation into progenitor cell populations in serum-free DMEM/F12 medium containing bFGF, ITS supplement and fibronectin. Neuronal differentiation of progenitor cells is further induced by withdrawal of bFGF from the culture medium [34, 37, 48]. Antibodies specific for various mature neuronal and glial phenotypes including serotonin, NeuN, MAP2C, β-III-tubulin and GFAP are applied to confirm the phenotype.

Example 7

Growth and Development of ST Infants

With spindle-chromosomal complex transfer, three pregnancies (one twin and two singletons) resulted from nine embryo transfers (33%). Four healthy infants were born including twins Monkey 1 and Monkey 2 and singletons Monkey 3 and Monkey 4. Animal growth rates based on weight for spindle-chromosomal complex transfer produced pregnancies are summarized in Table 1 and FIG. 1.

| Hematology Reference | Normal Range Juveniles 240 d-2 years | Spindle Transfer infants | | | |
|---|---|---|---|---|---|
| | | Monkey 1 315 days | Monkey 2 315 days | Monkey 3 253 days | Monkey 4 242 days |
| WBC | 3.8-12.6 | 13.1 | 16 | 7.1 | 17.4 |
| MPMN | 22.0-86.2% | 45.6 | 51.8 | 34.2 | 22.2 |
| IPMN | <0 | 0 | 0 | 0 | 0 |
| LYM | 7.4-70.5% | 49.4 | 40.2 | 60.4 | 71.9 |
| Mono | 1.4-7.7% | 3.5 | 5.5 | 2.8 | 3.9 |
| EOS | 0.8-3.6% | 0.7 | 1.5 | 2 | 0.7 |
| BA | 0.3-1.1% | 0.8 | 1 | 0.6 | 1.3 |
| RBC | 4.5-6.4 | 5.75 | 5.59 | 5.37 | 6.08 |
| PCV | 33.9-45.3% | 38.9 | 39.1 | 38 | 40.9 |
| HGB | 11.2-15.0 g/dl | 12.9 | 12.9 | 12.6 | 13.4 |
| MCV | 67-77 fL | 68 | 70 | 71 | 67 |
| MCH | 22.1-25.8 | 22.4 | 23.1 | 23.5 | 22 |
| MCHC | 32.2-34.0 g/dl | 33.2 | 33 | 33.2 | 32.8 |
| Platelets | 228-494 | 338 | 131 | 356 | 427 |

TABLE 2

Animal growth rates based on weights (kg) of rhesus monkey offspring produced by spindle-chromosomal complex transfer in comparison to infants from the timed mated breeding colony.

| ID# | | Birth weight | 1 | 2 | 3 | 4 | 5 | 6 | 7 | 8 | 9 | 10 |
|---|---|---|---|---|---|---|---|---|---|---|---|---|
| Controls | | | | | | | | | | | | |
| 28005 | control | 0.42 | 0.46 | 0.61 | 0.71 | 0.83 | 0.9 | 1 | 1.1 | 1.2 | 1 | 1.55 |
| 28019 | control | 0.5 | 0.59 | 0.6 | 0.8 | 1 | 1.2 | 1.2 | 1.3 | 1.4 | 1.4 | |
| 27939 | control | 0.58 | 0.8 | 0.85 | 0.94 | 1.2 | 1.2 | 1.6 | 1.7 | 1.8 | 2.04 | 2.01 |
| 28192 | control | 0.52 | 1 | 0.78 | 0.99 | 1.4 | 1.4 | 1.25 | 1.75 | 1.71 | | |
| 28084 | control | 0.54 | 0.64 | 0.6 | 0.8 | 1 | 1.2 | 1.13 | 1.1 | 1.4 | 1.45 | |
| 28085 | control | 0.42 | 0.64 | 0.52 | 0.6 | 0.71 | 0.79 | | 1.35 | 1.4 | 1.68 | 1.79 |
| AVERAGE | | 0.50 | 0.69 | 0.66 | 0.81 | 1.02 | 1.12 | 1.24 | 1.38 | 1.49 | 1.51 | 1.78 |
| St Error | | 0.03 | 0.08 | 0.05 | 0.06 | 0.1 | 0.09 | 0.1 | 0.12 | 0.09 | 0.17 | 0.13 |
| Spindle Transfer | | | | | | | | | | | | |
| 27956 | Monkey 3 | 0.5 | 0.6 | 0.7 | 0.8 | 1 | 1.2 | 1.4 | 1.6 | 1.7 | 1.9 | 2 |
| 28198 | Monkey 4 | 0.47 | 0.8 | 0.8 | 1 | 1.15 | 1.25 | 1.4 | 1.6 | 1.4 | 1.8 | |
| 27901 | Monkey 1 | 0.46 | 0.64 | 0.77 | 0.95 | 1.35 | 1.47 | 1.57 | 1.68 | 1.8 | 1.84 | 1.89 |
| 27902 | Monkey 2 | 0.35 | 0.53 | 0.7 | 0.87 | 1.25 | 1.44 | 1.57 | 1.7 | 1.6 | 1.76 | 1.75 |
| AVERAGE | | 0.45 | 0.64 | 0.74 | 0.91 | 1.19 | 1.34 | 1.49 | 1.65 | 1.63 | 1.83 | 1.88 |
| St Error | | 0.03 | 0.06 | 0.03 | 0.04 | 0.07 | 0.07 | 0.05 | 0.03 | 0.09 | 0.03 | 0.07 |

Numbered columns reflect the month number.

A cohort of control infants born from the time-mated breeding (TMB) colony was included for comparative purposes in an effort to assess possible procedure-related effects. No differences were noted between experimental monkeys born following mitochondrial gene replacement and controls. In addition, laboratory examination of the physical and chemical properties and components of blood was carried out. Analysis included number of red and white blood cells (erythrocytes and leukocytes); red cell volume, sedimentation (settling) rate, and hemoglobin concentration; cell shape and structure; hemoglobin and other protein structure; enzyme activity; and chemistry. All blood parameters for experimental animals were within the normal range for rhesus monkeys (Table 3).

Example 8

Additional Monkeys from Embryos Generated by Spindle Transfer

As described above, pregnancies were established from ST embryos created using SeV fusion. Cryopreserved oocytes are used to produce ST blastocysts for embryo transfer. ST embryos are cultured to blastocysts and then transferred into synchronized recipients, such as Japanese macaque or rhesus monkeys. In subsequent experiments ST embryos are transferred into recipients at the 4- or 8-cell stage to reduce detrimental effects of long-term in vitro culture. Synchronized recipients are selected based on ovarian cycles as determined by systemic estradiol levels (2 days post-ovulatory for the 4- or 8-cell stage embryos or 3-4 days for blastocysts). Two ST embryos are transferred per recipient by a laparoscopic approach with deposition into the oviduct. Intact ISCI embryos are sued as controls. Pregnancies are confirmed initially by monitoring endocrine profiles and later during gestation by ultrasonography.

Pregnancies proceed to term with delivery by C-section. However, one midgestation fetus is obtained and mtDNA heteroplasmy is analyzed in a variety of tissues and organs. In full-term infants, parentage analysis by microsatellite and mtDNA analysis is also performed. DNA samples are collected by non-invasive approaches involving the testing of placenta, cord blood, buccal smears, blood, skin (ear tissue sample), epithelial cell debris in urine and hair shaft/follicles. Leukocytes are isolated from the blood samples using commercially available kits.

As described above, a systematic examination of developmental and growth rates of ST infants is performed. Studies include measurements of body weight, size and body condition at birth, 1 month, 3 month of age and thereafter every 3 month as important indicators of health and early childhood survival. In addition, regular behavioral and neurologic examinations monitor reflexes, coordination, muscle strength and tonus.

One juvenile male and one female monkey are euthanized in order to allow extensive studies of tissue samples from brain, lung, heart, thyroid, thymus, liver, pancreas, spleen, kidney, small intestine, skeletal muscle and gonads. Cellular DNA will be extracted from collected samples to assess mtDNA heteroplasmy.

Example 9

Additional Methods, Non-Human Primates

Materials:
1. Recombinant human FSH, LH and CG (Ares Advanced Technologies Inc.; Norwell, Mass.) (or recombinant monkey gonadotropins when available)
2. Antide (GnRH antagonist, Ares Advanced Technologies Inc.)
3. Ketamine (Vedco, Inc., St. Joseph, Mo.)
4. TH3 medium: Hepes-buffered TALP medium, containing 0.3% BSA (6) Prepare medium by adding the indicated amounts of each reagent (Sigma, St. Louis, Mo.) to 1 L of Milli-Q water.

| | |
|---|---|
| NaCl | 6.660 g |
| KCl | 0.239 g |
| $CaCL_2$—$2H_2O$ | 0.294 g |
| $MgCl_2$·$6H_2O$ | 0.102 g |
| $Na_2HPO_4$ | 0.048 g |
| Glucose | 0.900 g |
| Na Lactate | 1.87 ml |
| Phenol Red | 0.010 g |
| $NaHCO_3$ | 0.168 g |
| Gentamicin sulfate | 0.050 g |
| Hepes | 2.603 g |
| Na Pyruvate | 0.060 g |
| pH | 7.2-7.4 |
| Osmolarity | 282 ± 10 |

Filter the medium using a 0.2µ filter unit and store for up to one month at +4° C. Add BSA (Sigma) at 3 mg/ml prior to use and refilter.

5. HECM-9 medium (7)
Prepare HECM-9 base medium by adding the indicated amounts of each reagent (Sigma) to 1 L of Milli-Q water.

| | |
|---|---|
| PVA | 0.1 g |
| NaCl | 6.639 g |
| KCl | 0.224 g |
| $CaCl_2$·$2H_2O$ | 0.279 g |
| $MgCl_2$·$6H_2O$ | 0.102 |
| $NaHCO_3$ | 2.1 g |
| Lactic Acid, Na salt, 60% syrup | 632 µl |
| Gentamicin sulfate | 0.01 g |
| pH | 7.2-7.4 |
| Osmolarity | 277 ± 5 |

Filter the medium using a 0.2 p filter unit and store for up to one week at +4° C.

Prepare 100× Amino Acid/Pantothenate stock by adding the indicated amounts of each reagent (Sigma) to 1 L of Milli-Q water.

| | |
|---|---|
| Taurine | 6.260 g |
| Asparagine | 0.130 g |
| Cysteine | 0.18 g |
| Histidine | 0.21 g |
| Lysine | 0.18 g |
| Proline | 0.12 g |
| Serine | 0.11 g |
| Aspartic Acid | 0.13 g |
| Glycine | 0.08 g |
| Glutamic Acid | 0.17 g |
| Glutamine | 2.92 g |
| Pantothenic Acid | 0.07 g |

Filter and aliquot 500 µl per 1.5 ml tubes and store at −20° C. for up to 3 months.

Add AA/Pantothenate stock to HECM-9 base medium at a ratio of 1:100 prior to use (HECM-9aa). HECM-9aa is used to hold oocytes from the time of recovery until IVF, ICSI or NT, as well as to culture embryos until the 4-8-cell stage (or Day 2). For extended culture (to the blastocyst stage), embryos are transferred at the 4-8-cell stage (end of Day 2) to HECM-9aa medium supplemented with 5% FBS (HyClone, v/v). Embryos are transferred to fresh HECM-9aa+ 5% FBS every other day.

6. D-sorbitol fusion medium (2)
Prepare fusion medium by adding the indicated amounts of each reagent (Sigma) to 1 L of Milli-Q water.

| | |
|---|---|
| D-Sorbitol | 46.378 g |
| Ca acetate | 0.0158 g |
| Mg acetate | 0.107 g |
| HEPES | 0.119 g |

Filter using a 0.2µ filter unit and store for up to one month at +4° C. Add fatty acid free BSA (Sigma) at 3 mg/ml prior to use and refilter.

7. Hyaluronidase (Sigma H-3506) stock: for 10× stock reconstitute 50 mg in 10 ml of Hepes-buffered TALP medium. Separate into 0.5 ml aliquots and store at −20° C.
8. Polyvinylpyrrolidone (PVP; Irvine Scientific; Santa Ana, Calif.). Reconstitute with 1 ml Hepes-buffered TALP medium prior to use.
9. $Ca^{2+}$- and $Mg^{2+}$-free Dulbecco's PBS (Invitrogen; Carlsbad, Calif.)
10. Cytochalasin B (Sigma C-6762, 1 mg) stock: to prepare 5 mg/ml (1000×) stock, reconstitute 1 mg cytochalasin B in 200 l of DMSO (Sigma). Aliquot at 5 µl per vial and store at −20° C.
11. Light paraffin oil (Zander IVF; Vero Beach, Fla.)
12. High viscosity silicon oil DC 200, 375 mPa·s (Fluka; Sigma-Aldrich).
13. at −20° C.
14. Micropipettes (Humagen; Charlottesville, Va.)
15. Cell strainers (70 µm Nylon; Falcon; BD Biosciences; Bedford, Mass.)
16. Patton Laparoscopic Catheter Introducer Set (Cook OB/GYN; Spencer, Ind.)
17. Portable incubator (Minitube of America, Verona, Wis.)
18. Ultrasonography equipment (OOWYCR, Philips)
19. Dissecting microscope (SZ-61, Olympus America, Inc.)
20. Restraint chair (Primate Products, Inc. Miami, Fla.)
21. Electrolyte cream (Reflux Creme, Hewlett Packard, Waltham, Mass.)
22. S5 Square Pulse Physiological Stimulator (Grass Instruments, Quincy, Mass.)
23. CCU 1 Constant Current Unit (Grass Instruments)
24. Disposable electrodes made by folding 6×7 cm piece of ordinary light weight aluminum foil six times lengthwise to produce a strip measuring 1×6 cm.
25. Inverted fluorescent microscope (IX-70 Olympus America, Inc.)
26. Micromanipulators (Joystick Oil Hydraulic MO-202D and Coarse MMN-1, Narishige International)
27. Inverted and dissecting microscope heating stages (ThermoPlate, TOKAI HIT CO., LTD. Japan) to provide temperature control at 37° C. during oocyte and embryo manuipulations.
28. Cell fusion equipment (BTX Electro Square Porator T820, BTX Instrument Division Harvard Apparatus, Inc., Holliston, Mass.)
29. Teflon Tubing (Inner diameter O.D.0.9 mm, Outer diameter O.D.2 mm, Narishige International)
30. Patton polyurethane transfer cannula (Cook OB/GYN)

Controlled Ovarian Stimulation (COS):
Protocols for COS in rhesus monkeys with recombinant human gonadotropins:
1. Monitor cycling females for menstruation and 1-4 days following onset, administer twice daily i.m injections of 30 IU recombinant human FSH (at 8 AM and 4 PM) for 8 days.
2. Administer Antide at a dose of 0.5 mg/kg, s.c. once a day for 8 days to suppress pituitary function and prevent spontaneous LH surges.
3. On the last two days of stimulation (days 7 and 8), additionally administer twice daily injections of recombinant human LH (30 IU i.m.).
4. On day 8, anesthetize animals with ketamine (10 mg/kg body weight, i.m) and examine ovarian morphology by ultrasonography. Typically, a responsive ovary will be enlarged from 6 mm to an average diameter of 10 mm or greater and will contain at least 5 large follicles, 2-4 mm in diameter.
5. On the morning of day 9, inject monkeys meeting these criteria with recombinant hCG (1000 IU, i.m.) to induce oocyte maturation. Ovarian oocytes, which arrest at prophase I (GV), resume meiosis in response to hCG and arrest again at metaphase II (MII). Approximately 20% of gonadotropin-treated females are discontinued at this time due to lack of adequate response as judged by ultrasonography.

Laparoscopic Oocyte Recovery:
Oocytes are collected by laparoscopic follicular aspiration 27-33 h after hCG injection (9) via transabdominal needle aspiration of gravid ovarian follicles. Laparoscopy plays a prominent role in the IVF laboratory, with most surgical procedures accomplished by this methodology.
1. Anesthetize monkeys with isoflurane gas vaporized in 100% oxygen. Comprehensive physiologic monitoring of animals should be conducted throughout the surgery, including ECG, peripheral oxygen saturation, and end-expired carbon dioxide. Orotracheal intubation and mechanical ventilation to maintain expired $CO_2$ at less than 50 mm Hg is mandatory.
2. Perform sterile skin preparation and draping after which the abdomen is insufflated with $CO_2$ at 15 mm Hg pressure. Insert the viewing telescope via a small supraumbilical incision, with accessory ports placed in the paralumbar region.
3. Position the monkey in Trendeleburg, allowing the viscera to migrate in a cephalad direction exposing the reproductive organs.
4. Use a single small grasping forceps to stabilize the ovary for examination and needle aspiration. Rarely is a second accessory port and grasping forceps required for the experienced laparoscopist to perform this procedure.
5. After mobilization of the ovary, connect a 22 g hypodermic needle to a source of continuous vacuum (−120 mm Hg), and insert into individual follicles until all have been aspirated.
6. Reduce insufflation and close the incisions with interrupted absorbable suture in an intradermal pattern.
7. Place tubes containing follicular aspirates into a portable incubator (Minitube) at 37° C. and transport quickly to the lab (See Note 2).
8. Add 10× hyaluronidase stock solution directly to the tubes containing aspirates at 1:10 ratio and incubate at 37° C. for 30 sec.
9. Gently agitate the contents with a serological pipette to disaggregate cumulus and granulosa masses and pour the entire aspirate onto a cell strainer.
10. Oocytes are retained in the mesh, while blood, cumulus and granulosa cells are sifted through the filter
11. Quickly backwash the strainer with TH3 medium and collect the medium containing oocytes in a Petri dish.
12. Rinse oocytes, which are now easily identified in TH3 medium.
13. Any remaining cumulus cells can be removed by manual clean up with a small bore pipette (approximately 125 um in inner diameter).
14. Oocytes can be observed at higher magnification for determination of their developmental stage (GV, MI or MII) as well as quality (granularity, shape and color of the cytoplasm). On average, 40 oocytes are collected per stimulation, with over 70% matured or maturing (MII and MI stages).
15. After evaluation, transfer oocytes into chemically defined, protein-free HECM-9aa medium (7) at 37° C. in 5% $CO_2$, until further use. Most MI stage oocytes should mature to the MII stage within 3-4 hours.

Collection of Spermatozoa:
Penile electroejaculation provides a consisted, successful, and humane method for the collection of semen in the rhesus monkey. Pregnancy-proven males assigned to electroejaculation must be evaluated on the basis of ease of restraint, number of attempts required to obtain a sample and the animals' tolerance of the procedure (See note 3).

1. Transfer animal to the restraining chair and secure by tying arms and legs with leather straps to the chair. The belly band restrainer can be useful on new animals to lessen animal movements.
2. Apply electrolyte cream to the entire shaft of the penis with the exception of the glans. Wrap one electrode around the base of the penis with the excess length folded to create a tab to which the negative stimulator lead is connected. Position the second electrode immediately behind the glans and connect to the positive stimulator lead.
3. With the electrodes attached, gently grasp the penis between the index and second finger, extent slightly and position over a sterile 10 ml glass beaker.
4. Set the CCU 1 Constant Current unit output switch to NORMAL and the Current Adjustment dial to zero. At these settings the animal receives about one milliampere of current. This low current prepares the animal for the procedure, in a process called priming (See note 4).
5. Adjust the S5 Square Pulse Stimulators Frequency setting to 17 pulses/sec and a Duration setting of 17 milliseconds with Multiply switches on both setting at ×1. Set the maximum Volt levels (80) with Multiply switch at ×10.
6. Increase the Current Adjustment switch on CCU 1 gradually from 0 to a setting of 4-4.5 until collecting the sample. Never go beyond a setting of 5.
7. Continue to stimulate the animal until a sample is obtained but never go beyond 20 seconds (See note 5).
8. Turn off the Constant Current output by moving Output Adj I on CCU 1 Unit to the off position after obtaining a sample, or after a total stimulus time of 30-35 seconds (if priming time is added) per trial or less.
9. Allow the ejaculate to liquefy at room temperature for approximately 15 minutes before processing Enucleation and Karyoplast Isolation
1. Transfer MII oocytes to 300 manipulation droplets of TH3 with 5 µg/ml cytochalasin B on a glass bottom manipulation dish (www.willcowells.com) covered with paraffin oil (Zander IVF) and incubate at 37° C. for 10-15 min before spindle removal. (See note 8).
2. The micromanipulation tool set up is similar to that described for the ICSI procedure bellow except that a larger, beveled, enucleation pipette (20-25 um outer diameter) is used.
3. Completely fill the enucleation pipette with high viscosity silicon oil to improve control over aspiration and injection.
4. Mount the manipulation chamber with oocytes on an inverted microscope (Olympus) equipped with the OOSIGHT™ Imaging System (CR1, Inc.), XYClone or the ZILOS-TK™ laser objective (Hamilton Thorne, Inc.), glass stage warmer (Tokai Hit, www.tokaihit.com) and Narishige micromanipulators.
5. Visualize the metaphase spindle usually adjacent to the polar body using OOSIGHT spindle imaging system.
6. Immobilize an individual oocyte using the holding pipette with the spindle positioned at 1-3 o'clock and lower the holding pipette with attached oocyte slightly until it touches the bottom of the plate to stabilize the egg during enucleation.
7. Bring the enucleation pipette into sharp focus position with its beveled bore opening positioned toward the spindle.
8. Make a small hole in the on a pellucid using a laser pulse.
9. Slowly insert the pipette through the zona pellucida opening without piercing the plasma membrane.
10. Once the zona is penetrated, bring the pipette tip close to the spindle and slowly aspirate the spindle with as little as possible the underlying cytoplasm into the enucleation pipette.
11. Confirm the presence of the spindle in the pipette under spindle imaging optics.
12. If the spindle is still in the egg, navigate the enucleation pipette to the spindle under OOSIGHT ensuring that the tip of pipette and the spindle are brought to the same focal plane.
13. After aspirating the spindle into the enucleation pipette, withdraw the pipette slowly from the slit in the zona pellucida.
14. Place isolated karyoplasts containing spindles and enucleated oocytes in separate microdrops before further manipulation.

Spindle Transfer
1. Aspirate a karyoplast into the same enucleation pipette and transfer into a drop containing an extract of Sendai virus (GENOMONE™ kit, Cosmo Bio. Co. Ltd.).
2. Expel the karyoplast into the extract buffer and pipette by repeated aspiration and expelling.
3. Aspirate a karyoplast into the pipette with a small amount of the Sendai extract and transfer the pippete into a separate drop containing enucleated oocytes.
4. Drill a small hole in the zona pellucida on opposite side to the $1^{st}$ polar body using the laser objective
5. Insert the pipette through the zona opening and expel the karyoplast into the perivitelline space ensuring a close contact between the cell membranes.
6. Place manipulated oocytes into culture dishes containing HECM medium and incubate at 37 C in 5% $CO_2$, for 15-30 minute until fusion
7. Confirm successful fusion visually by the disappearance of the karyoplast in the perivitelline space.

Fertilization by Intracytoplasmic Sperm Injection (ICSI) and Embryo Culture:

ICSI is a robust efficient fertilization procedure in the monkey resulting in high pronuclear formation rates (80-90%).
1. Wash collected spermatozoa twice by resuspending with TH3 medium followed by centrifugation of the liquid portion of the ejaculate for 7 min, at 200×g.
2. Take an aliquot and determine motility and concentration before the final centrifugation and resuspension step.
3. Adjust sperm concentration to $1 \times 10^6$ motile spermatozoa per ml in TH3 medium and store for approximately 3 h at room temperature prior to ICSI.
4. The ICSI procedure is carried out on an inverted microscope equipped with Hoffman or Relief contrast optics, heating stage (set at 37° C.) and micromanipulators.
5. Immobilize an oocyte using a holding pipette (120-130µ outer and 25-40µ inner diameter) attached to a micropipette holder (Narishige) and controlled by air filled teflon tubing connected to a 20 ml plastic syringe (Becton Dickinson).
6. Fill approximately half the holding micropipette with TH3 medium prior to the micromanipulation procedure.
7. Fill the ICSI micropipette completely with light paraffin oil and then attach it to a Milli-Q water filled Narishige pipette holder and teflon tubing that extends to a 200 µl volume Hamilton microsyringe controlled by a microinjector (Narishige). The line, microsyringe and ICSI micropipette must be completely free of air bubbles.
8. After setting up and positioning the micropipettes, dilute a small aliquot of sperm with 10% polyvinylpyrrolidone (1:4) and place a 5 μl drop in a micromanipulation chamber; usually the lid of a Falcon 1006 Petri dish.
9. Place a 30 μl drop of TH3 in the same micromanipulation chamber next to the sperm droplet and ensure both are covered with paraffin oil.
10. Place the oocytes into the micromanipulation drop and mount the chamber on the stage of the microscope.
11. Lower the ICSI pipette into the sperm drop and select a motile sperm which is immobilized by striking the midpiece with the tip of the pipette, and slowly aspirated into the pipette tail first.
12. Move the injection pipette to the manipulation drop containing oocytes.
13. Lower the holding pipette into the manipulation drop and immobilize an individual oocyte with the polar body positioned at either 12 or 6 o'clock.
14. Slightly lower the holding pipette with oocyte attached until it touches the bottom of the plate to stabilize the egg during injection.
15. Bring the ICSI pipette into sharp focus at the 3 o'clock position and slowly push the sperm to the pipette tip using the Hamilton microsyringe.
16. Pierce the ICSI pipette through the zona pellucida and inject the sperm into the cytoplasm of the oocyte, away from the polar body, making sure that the pipette completely breaks through the plasma membrane and that the sperm is deposited with a minimal amount of medium.
17. After ICSI, place injected oocytes in 4-well dishes containing pre-equilibrated HECM-9aa medium and culture at 37° C. in 5% $CO_2$, 5% $O_2$ and 90% $N_2$. Maintain cultures under paraffin oil throughout the culture period.
18. Assess fertilization 12-14 hours after injection by the presence of pronuclei.
19. At the 8-cell stage transfer embryos to fresh dishes of HECM-9aa medium supplemented with 5% fetal bovine serum and culture for a maximum of 7 days with observation/scoring and medium change every other day (See note 7).

Embryo Transfer:

Adult, multiparous females monitored for mense are used as recipients. Daily blood samples are collected beginning on day 8 of the menstrual cycle and serum levels of estradiol are quantitated by RIA. The day following the peak in serum estradiol is considered the day of ovulation (day 0). The pregnancy success rate depends on the synchrony between the age of the transferred embryos, as measured by culture time in vitro, and the host endometrium, relative to the predicted day of ovulation. The optimal timing for blastocyst (day 6/7) transfer is into a day 4 uterine environment, while cleavage stage embryos at a culture age of 1-4 days can be optimally transferred into a day 2 recipients.

Recipient females within 1 to 4 days of ovulation are anesthetized with ketamine, and prepared for laparoscopic embryo transfer utilizing the same basic laparoscopic approach and anesthesia as described for follicular aspiration.
1. Examine the ovaries with a self retaining micro retractor inserted at a high paramedian position after insertion of the telescope and Trendeleburg positioning.
2. Transfer embryos preferentially into the oviduct with an ovulation site on the associated ovary.
3. Grasp the fimbria with a Patton retractor and place in traction.
4. Insert the Patton cannula transabdominally and advance through the fimbria into the oviduct to a distance of 1-3 cm.
5. Typically, transfer two ICSI or IVF embryos to the oviduct of the recipient.
Remove embryos from culture medium and transfer to a dish containing TH3 medium.
6. Connect the transfer catheter to a 1 ml syringe filled with about 0.01-0.02 ml of TH3 medium avoiding air bubbles.
7. Carefully load embryos near the catheter tip with a total volume not exceeding 0.03 ml.
8. Insert the catheter into the external orifice of the cannula and advance into the oviduct to a depth of 1-3 cm and deposit the embryos.
9. Carefully examine the catheter following transfer to ensure that all embryos have been transferred. If an embryo has been retained it can be subjected to a second transfer attempt.
10. The skin incision closure is identical to the follicle aspiration procedure described previously.

To detect pregnancy, serum levels of estrogen and progesterone are monitored every third day after embryo transfer. Pregnancy is confirmed by ultrasound approximately 25 days post-transfer and monitored periodically throughout gestation.

It will be apparent that the precise details of the methods or compositions described may be varied or modified without departing from the spirit of the described invention. We claim all such modifications and variations that fall within the scope and spirit of the claims below.

The invention claimed is:

1. A method for producing an oocyte in vitro comprising the steps of:
   (a) enucleating a recipient primate oocyte arrested at metaphase II from a first primate in a manner that does not lower levels of maturation promoting factor (MPF) to form an enucleated recipient primate oocyte, wherein the recipient primate oocyte is enucleated using a non-UV-based spindle imaging system; and
   (b) isolating nuclear genetic material comprising chromosomes from a donor primate oocyte arrested at metaphase II from a second primate and introducing into the enucleated recipient primate oocyte, wherein introduction of the chromosomes is performed using a fusogenic agent, wherein the fusogenic agent is Sendai virus, and wherein the first primate and the second primate are from the same primate species, thereby producing a hybrid oocyte arrested at metaphase II, wherein the hybrid oocyte can be can be fertilized.

2. The method of claim 1, further comprising
   (c) fertilizing the hybrid oocyte in vitro to form a one-celled embryo that is totipotent and (i) is capable of four or more cell divisions; (ii) maintains a normal karyotype while in culture; (iii) is capable of differentiating into trophectoderm, germ cells, ectoderm, mesoderm, and endoderm layers; and (iv) comprises mitochondrial DNA derived from the first primate and nuclear genetic material derived from the donor primate oocyte of a second primate.

3. The method of claim 2, further comprising
   (d) culturing the one-celled embryo in vitro, wherein the one celled embryo divides, thereby producing a two-celled embryo, four-celled embryo, eight-celled embryo, a morula or a blastocyst.

4. The method of claim 3, wherein the method produces an eight-celled embryo with an efficiency of greater than about 90%.

5. The method of claim 3, further comprising
   (e) implanting the one-celled embryo, two-celled embryo, four-celled embryo, eight-celled embryo, morula, or blastocyst embryo into the first primate.

6. The method of claim 3, further comprising
   (f) implanting the one, two, four eight celled embryo, morula, blastocyst or any other preimplantation stage embryo into a surrogate primate of the same species as the embryo, wherein the surrogate primate is not the donor or the recipient primate.

7. The method of claim 1, wherein the first primate and the second primate are non-human.

8. The method of claim 1, wherein the donor primate oocyte is from a female subject with a mitochondrial disease.

9. The method of claim 8, wherein the mitochondrial disease is a homoplasmic mitochondrial disease associated with infertility.

10. The method of claim 8, wherein the mitochondrial disease is Leber's hereditary optic neuropathy, myoclonic epilepsy, or Kearns-Sayre Syndrome.

11. The method of claim 6, further comprising allowing the surrogate primate to carry the embryo to term.

12. The method of claim 2, further comprising culturing the one-celled embryo to form a blastocyst.

13. The method of claim 1, wherein the donor primate oocyte, the recipient primate oocyte, or both have been frozen and thawed.

14. A method for producing an oocyte in vitro comprising the steps of:
   (a) enucleating a recipient primate oocyte from a first primate without a mitochondrial disease in a manner that does not lower levels of maturation promoting factor (MPF), wherein the primate oocyte is enucleated using a non-UV-based spindle imaging system;
   (b) isolating a karyoplast comprising chromosomes from nuclear donor primate oocyte arrested at metaphase II from a second primate with a mitochondrial disease
   (c) introducing the karyoplast into the enucleated recipient primate oocyte, wherein introduction of the karyoplast is performed using a fusogenic agent, wherein the fusogenic agent is Sendai virus, and wherein the first primate and the second primate are from the same primate species, but wherein the first primate does not have the mitochondrial disease, thereby producing a hybrid oocyte that is arrested at metaphase II;
   (c) fertilizing the hybrid oocyte in vitro to produce a one-celled embryo; and
   (d) culturing the one-celled embryo in vitro to form a two-, four- or eight-celled embryo, a morula or a blastocyst embryo.

15. The method of claim 14, further comprising transferring the embryo into the recipient primate, and allowing the recipient primate to carry the embryo to term.

16. The method of claim 14, wherein the donor primate oocyte, the recipient primate oocyte, or both have been frozen and thawed.

* * * * *

UNITED STATES PATENT AND TRADEMARK OFFICE
CERTIFICATE OF CORRECTION

PATENT NO. : 9,434,921 B2
APPLICATION NO. : 13/265326
DATED : September 6, 2016
INVENTOR(S) : Shoukhrat Mitalipov It is certified that error appears in the above-identified patent and that said Letters Patent is hereby corrected as shown below:

In the Specification

At Column 1, Lines 16-19, under the heading STATEMENT OF GOVERNMENT SUPPORT and above the heading FIELD, please delete the following paragraph:
"This invention was made with United States government support pursuant to grant RR00163 from the National Institutes of Health (NIH); the United States government has certain rights in the invention."

And replace it with the following:
-- This invention was made with government support under P51 RR000163 and U54 HD018185 awarded by the National Institutes of Health. The government has certain rights in the invention. --

Signed and Sealed this
Ninth Day of July, 2019

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
taacatatcc gatcagagcc                                                   20
```

```
<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
ttaaacaccc tctacgccg                                              19
```